US011236360B2

(12) United States Patent
Schmidt

(10) Patent No.: US 11,236,360 B2
(45) Date of Patent: Feb. 1, 2022

(54) ADENO-ASSOCIATED VIRUSES ENGINEERED FOR SELECTABLE TROPISM

(71) Applicant: Regents of the University of Minnesota, Minneapolis, MN (US)

(72) Inventor: Daniel Schmidt, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 589 days.

(21) Appl. No.: 15/836,345

(22) Filed: Dec. 8, 2017

(65) Prior Publication Data

US 2018/0208943 A1 Jul. 26, 2018

Related U.S. Application Data

(60) Provisional application No. 62/432,467, filed on Dec. 9, 2016.

(51) Int. Cl.
| | |
|---|---|
| *C12N 15/86* | (2006.01) |
| *C07K 14/00* | (2006.01) |
| *C07K 16/18* | (2006.01) |
| *C07K 16/28* | (2006.01) |
| *C12N 7/01* | (2006.01) |
| *C07K 14/435* | (2006.01) |
| *C07K 14/46* | (2006.01) |
| *C12N 15/10* | (2006.01) |
| *A61K 48/00* | (2006.01) |
| *C07K 14/005* | (2006.01) |

(52) U.S. Cl.
CPC .......... *C12N 15/86* (2013.01); *A61K 48/0008* (2013.01); *C07K 14/00* (2013.01); *C07K 14/005* (2013.01); *C07K 14/43518* (2013.01); *C07K 14/46* (2013.01); *C12N 15/1082* (2013.01); *C12N 15/1093* (2013.01); *C07K 2319/02* (2013.01); *C07K 2319/20* (2013.01); *C07K 2319/21* (2013.01); *C07K 2319/42* (2013.01); *C07K 2319/55* (2013.01); *C07K 2319/60* (2013.01); *C07K 2319/70* (2013.01); *C12N 2750/14122* (2013.01); *C12N 2750/14145* (2013.01); *C12N 2750/14151* (2013.01); *C12N 2750/14171* (2013.01)

(58) Field of Classification Search
None
See application file for complete search history.

(56) References Cited

U.S. PATENT DOCUMENTS

| | | | |
|---|---|---|---|
| 9,193,956 B2 | 11/2015 | Schaffer et al. | |
| 2009/0215870 A1* | 8/2009 | Terwilliger | C12N 15/86 514/44 R |
| 2013/0224756 A1* | 8/2013 | Cohen | C07K 14/00 435/6.17 |
| 2014/0056854 A1 | 2/2014 | Asokan et al. | |
| 2018/0230489 A1* | 8/2018 | Kotin | A61K 35/76 |

FOREIGN PATENT DOCUMENTS

| | | | |
|---|---|---|---|
| EP | 2692731 A1 | | 2/2014 |
| WO | WO-97/38723 A1 | | 10/1997 |
| WO | WO-2006/105392 A2 | | 10/2006 |
| WO | WO 2006119150 | * | 11/2006 |
| WO | WO-2010/093784 A2 | | 8/2010 |

OTHER PUBLICATIONS

Chen et al, Fusion Protein Linkers: Property, Design and Functionality, Adv Drug Deliv Rev. Oct. 15, 2013; 65(10): pp. 1-32.*
Hagen et al, Modular adeno-associated virus (rAAV) vectors used for cellular virus-directed enzyme prodrug therapy, Scientific Reports, 2013, pp. 1-11.*
Hemminki et al, Targeting Oncolytic Adenoviral Agents to the Epidermal Growth Factor Pathway with a Secretory Fusion Molecule, Cancer Research 61, 6377-6381, Sep. 1, 2001.*
Wu, Pei, et al., "Mutational Analysis of the Adeno-Associated Virus Type 2 (AAV2) Capsid Gene and Construction of AAV2 Vectors with Altered Tropism", *Journal of Virology*, 74(18), (2000), 8635-8647.

* cited by examiner

*Primary Examiner* — Maria Marvich
(74) *Attorney, Agent, or Firm* — Schwegman Lundberg & Woessner, P.A.

(57) ABSTRACT

Methods to prepare recombinant adeno-associated virus (AAV) capsids with altered tropism and compositions having AAVs with altered tropism are provided.

20 Claims, 9 Drawing Sheets

Specification includes a Sequence Listing.

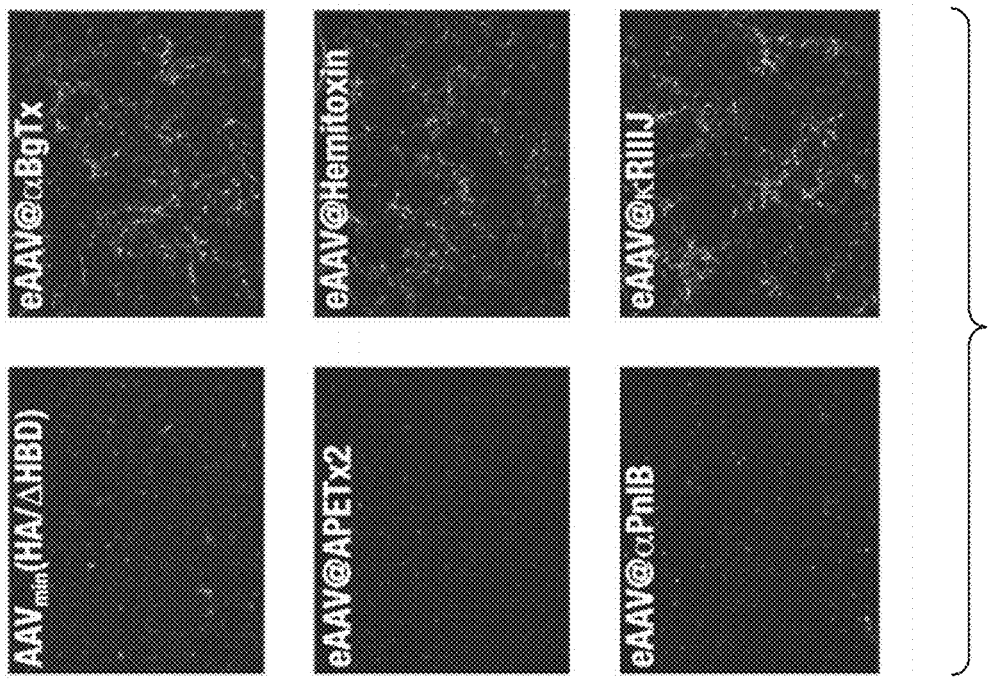
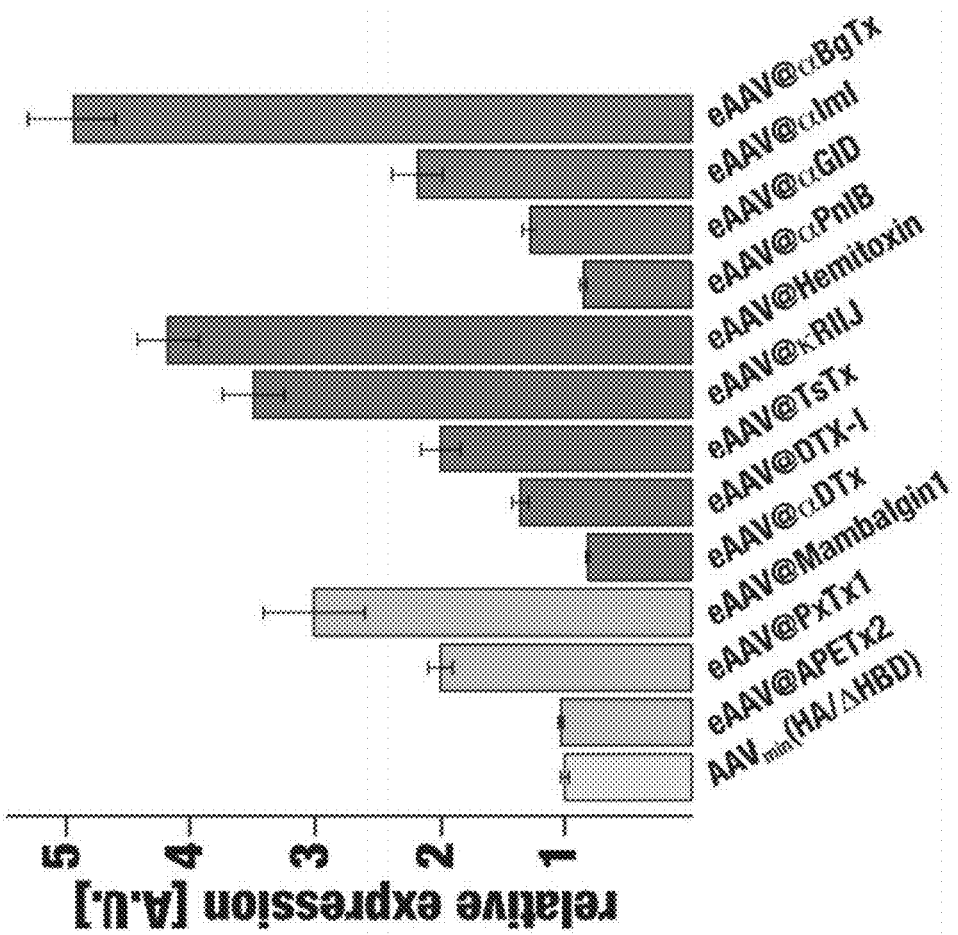
Fig. 5A
Fig. 5B

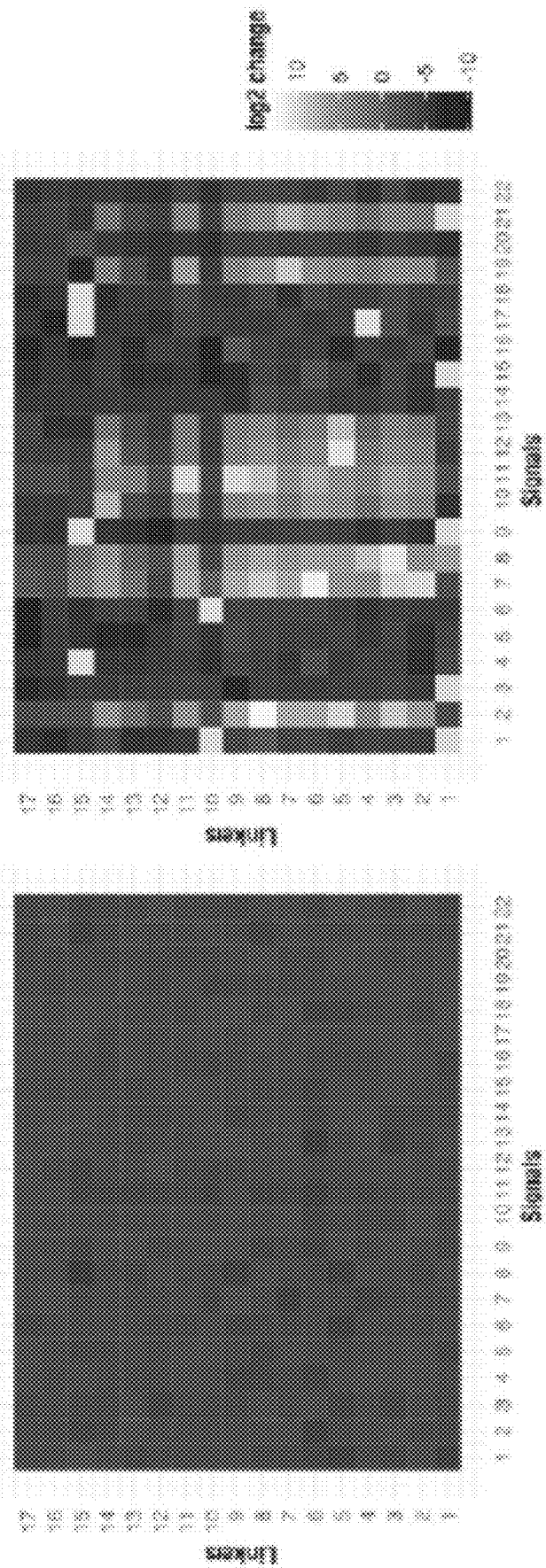

ADENO-ASSOCIATED VIRUSES ENGINEERED FOR SELECTABLE TROPISM

CROSS-REFERENCE TO RELATED APPLICATIONS

This application claims the benefit of the filing date of U.S. application Ser. No. 62/432,467, filed on Dec. 9, 2016, the disclosure of which is incorporated by reference herein.

STATEMENT OF GOVERNMENT RIGHTS

The invention was made with U.S. government support under grant MH109038 awarded by the National Institutes of Health. The Government has certain rights in the invention.

FIELD OF THE INVENTION

A viral gene delivery platform that removes legacy constraints of natural evolution by engineering biomedically relevant properties into adeno-associated virus (AAV) to improve cell-type specificity.

BACKGROUND

There is a long history of rational engineering of AAV capsid proteins to redirect tropism towards more specific targets. Many of these efforts involved short (about 7 amino acids) peptides being inserted into capsid proteins loops, an approach called viral display. However, this approach requires extensive screening for high affinity/avidity variants that are target specific. Given the small interaction footprint that is possible with short peptide stretches this has proven problematic. Other approaches are to display more complex proteins on the virus capsid (e.g. DARPIN, Affibodies). However, these scaffolds have to be rendered target specific through directed protein evolution. Similarly, attempts to display on AAV capsid proteins, such as single chain antibodies (scFv) that are already in clinical use as biologics treating a variety of conditions (e.g., cancer), have had limited success due the challenging biochemistry of these proteins. They contain disulfide bonds, which need to form in specific ways as the recombinant scFV-AAV capsid fusion is made to be functional for binding.

SUMMARY

This disclosure resolves the mismatch between naturally evolved properties of commonly used viral vectors, specifically their broad tropism, and the need for greater gene delivery specificity required by a disease's pathology. This disclosure addresses the shortcomings in two ways: A) Instead of displaying scaffolds (DARPIN, scFV, etc.) that first have to be engineered to target relevant surface receptor on specific cell types, we are using complex peptides from venomous animals (peptide toxins). Peptide toxins have evolved to bind surface-exposed targets involved in cellular signaling with extremely high affinity and fidelity. They can distinguish between closely related members of the same family with almost perfect discrimination and so can be employed in genetically-encoded engineered proteins; and B) Peptide toxins generally contain several cysteines and thus can be as hard-to-fold as antibodies and scFV when produced in recombinant expression systems. The present disclosure provides for the use of specific cellular signals that route the nascent peptide toxin/AAV capsid fusion proteins through specific cellular compartments that are providing the right environment (oxidizing, access to chaperones, etc.) so that they can achieve a functional fold when expressed in recombinant expression systems.

In one embodiment, a method to prepare recombinant adeno-associated viruse (AAV) capsids with altered tropism is provided. The method includes providing one or more vectors having DNA encoding one or more polypeptide toxins or peptides of the toxin (hereinafter both the full-length polypeptide and peptides of the toxin are referred to as "peptide of a toxin"), one or more vectors having DNA encoding one or more peptide sorting signals, e.g., secretion signals, nuclear import signals or Golgi retention signals, one or more vectors having DNA encoding one or more peptide linkers, and one or more vectors having DNA encoding VP2 of AAV; and combining in a ligation reaction the DNA encoding one or more peptides of a toxin, the DNA encoding one or more peptide sorting signals, the DNA encoding one or more peptide linkers, the DNA encoding the VP2 of AAV, and a host vector, thereby providing a ligated library of host vectors which includes a host vector having an open reading frame comprising the DNA encoding one or more peptide sorting signals linked to the DNA encoding one or more peptides of a toxin linked to the DNA encoding one or more peptide linkers linked to the DNA encoding the VP2. In one embodiment, the ligation reaction further comprises DNA encoding a tag, e.g., a His-tag, useful to isolate or purify virions. In one embodiment, the AAV is AAV1, AAV2, AAV5, AAV6, AAV8, AAV9, AAV100, or AAV-DJ (Grimm et al. (2008). In one embodiment, the heparin binding domain (HBD) or laminin binding domain in VP2 is deleted or mutated to decrease binding to proteoglycans. In one embodiment, the toxin binds to a molecule displayed on the surface of a eukaryotic cell, including but not limited to K+ channels (voltage-dependent, ligand-gated, mechanically gated, and leak channels), Na+ channels (voltage-dependent, ligand-gated, mechanically gated, and leak channels), Ca2+ channels (voltage-dependent, ligand-gated, mechanically gated, and leak channels), H+ channels (voltage-gated), Cl– channels, anionic Cys-loop receptors (ligand-gated ion channels GABA(A), GlyR), cationic Cys-loop receptors (ligand-gated ion channels nAChR, 5-HT), ionotropic glutamate receptors (ligand-gated ion channels AMPA, Kainate, NMDA receptors), ATP-gated channels (P2X receptors), or class C GPCRs (including metabotropics glutamate receptors), e.g., an ion channel protein or G-protein coupled receptor (GPCR), e.g., alpha2-adrenoceptor. In one embodiment, the cells are further contacted with one or more vectors encoding a recombinant AAV genome, adenovirus helper proteins E2A, E4 and VA, and AAV VP1 and VP3, so as to produce helper-free AAV with altered tropism. In one embodiment, the DNA encoding the peptide of a toxin encodes a peptide of a toxin that 200 or less than 200, e.g., 150, 100, 50 or 25, such as from about 20 or 40 to about 100, amino acids in length. In one embodiment, the host vector has DNA encoding peptide linker. In one embodiment, the DNA encoding the linker has less than about 500, e.g., 400, 300, 200, 150, 100, 75, 50, 40, 30, 20, 10, or 5, e.g., from about 4 to about 50 to 100, amino acids in length. In one embodiment, the host vector has DNA encoding a sorting signal. In one embodiment, the DNA encoding the sorting signal has less than 50, e.g., 40, 35, 30, 25, 200 or 25, such as from about 15 to about 40, amino acids in length. A ligated library produced by the method is also provided, as well as a composition comprising helper-virus free recombinant AAV (rAAV) comprising a capsid protein comprising a peptide of a toxin linked to VP2, and a recombinant AAV genome is provided.

In one embodiment, a method to prepare recombinant AAV with altered tropism is provided. In one embodiment, the method includes providing a cell having a nucleic acid having a rAAV genome, AAV VP1 and VP3 and adenovirus E2A, E4 and VA; and contacting the cell with a host vector having an open reading frame comprising a DNA encoding one or more peptide sorting signals linked to a DNA encoding one or more peptides of a toxin linked to a DNA encoding one or more peptide linkers linked to a DNA encoding the VP2 an amount that generates helper-free rAAV with altered tropism. In one embodiment, the rAAV genome is provided to the cell by contacting the cell with a vector having the genome before or at the same time as the host vector. In one embodiment, the VP1, VP3, E2A, E4, VA, or any combination thereof is provided by contacting the cell with one or more vectors encoding VP1, VP3, E2A, E4, or VA. In one embodiment, the peptide is a peptide of PcTx1, Mambalgin, APETx2, μO-CNTX MrVIB, μ-CNTX SIIIA, ProTx-I, Pterinotoxin, VSTXe, αDTX, DTX-I, Hemitoxin, κ-CNTX RIIJ, TsTX-K-α, or α-BGTx(V31 isoform). In one embodiment, the sorting signal comprises MGWSCIILFLVATATGAHS (SEQ ID NO: 1), MSTMRLLTLALLFSCSVA (SEQ ID NO:2), MSTMHLLTFALLFSCSFARA (SEQ ID NO:3), MQHIFAFFCTGFLGAVVG (SEQ ID NO:4), MKPSAECCSPKFWLVLAVLAVSGSKA (SEQ ID NO:5), MSALLILALVGAAVA (SEQ ID NO:6), MDVCVRLALWLLWGLLLHQGQS (SEQ ID NO:7), MKLCILLAVVAFVGLSLG (SEQ ID NO:8), MKLSLVAAMLLLLSAARA (SEQ ID NO:9), MLLSVPLLLGLLGLAVA (SEQ ID NO:10), MQKIMHISVLLSPVLWGLIFGVSS (SEQ ID NO: 11), MKTIIALSYIFCLVFA (SEQ ID NO:12), MRCSPGGVWLALAASLLHVSLQ (SEQ ID NO:13), MATGSRTSLLLAFGLLCLPWLQEGSA (SEQ ID NO:14), MDSKGSSQKGSRLLLLLVVSNLLLCQGVVS (SEQ ID NO:15), MWPLVAALLLGSACCGSA (SEQ ID NO:16), MVCFRLFPVPGSGLVLVCLVLGAVRSYA (SEQ ID NO: 17), MRLAVGALLVCAVLGLCLA (SEQ ID NO: 18), MRGTPLLLVVSLFSLLQD (SEQ ID NO:19), MGLRALMLWLLAAAGLVRESLQG (SEQ ID NO:20), MDYGGALSAVGRELL (SEQ ID NO:21), MPPLLAPLLCLALLPALA (SEQ ID NO:22), or MGAMAPRTLLLLLAAALAPTQRA (SEQ ID NO:23), or a fragment thereof with substantially the same activity as one of SEQ ID NO: 1-23. In one embodiment, the linker comprises GSAG (SEQ ID NO:24), GSAGSAG (SEQ ID NO:25), GSAGSAGSAG (SEQ ID NO:26), GSAGSAGSAGGSAGSAGSAG (SEQ ID NO:27), AAADYKDDDDKIDAAAGGALCN (SEQ ID NO:28), IDYKDDDDKLAAAGNGNGNGNGNGNGNGDGNGGALCN (SEQ ID NO:29), PPPPPPPPPPPPPP (SEQ ID NO:30), GNGN (SEQ ID NO:31), GNGNAGNGN (SEQ ID NO:32), GNGNAGNGNAGNGNAGNGN (SEQ ID NO:33), AEAAAKA (SEQ ID NO:34), AEAAAKEAAAKA (SEQ ID NO:35), AEAAAKEAAAKEAAAKA (SEQ ID NO:36), AEAAAKEAAAKEAAAKEAAAKA (SEQ ID NO:37), PDANLRPEDLW (SEQ ID NO:38), PDANLRPEDLWANHSKVV (SEQ ID NO:39), PDANLRPEDLWANHSKVVPLPKPPHMKDSA (SEQ ID NO:40), EEEEKKKQQEEEAERLRRIQEEMEKERKRREDEKRRRKEEEERRMKLEME AKRKQEEEERKKREDDEKRKKK (SEQ ID NO:41), EEEEKKKEEEEKKQKEEQERLAKEEAERKQKEEQERLERERKEREEQEKKAKEEAERIAKLEAEKKAEEERKAKEEEEERKAKEEEERKKKEEQERLAKEKEE AERKAAEEKKAKEEQERKEKEEAERKQR (SEQ ID NO:42), or EEEEKKKEEEEKKQKEEQERLAKEEAERKQKEEQERLAKEEAERKQKEEEE RKQKEEEERKQKEEEEERKLKEEQERKAAEEKKAKEEAERKAKEEQERKAE EERKKKEEEEERLERERKEREEQEKKAKEEAERIAKLEAEKKAEEERKAKEE EERKAKEEEEERKKKEEQERLAKEKEEAERKAAEEKKAKEEQERKEKEEAE RKQR (SEQ ID NO:43) or a fragment thereof. In one embodiment, the toxin binds a GPCR or a chloride channel, e.g. a toxin such as three-finger muscarinic toxin 7 (LTCVKSNSIWFPTSEDCPDGQNLCFKRWQYISPRMYDFTRGCAATCPKAEY RDVINCCGTDKCNK; SEQ ID NO:44) or a fragment thereof or chlorotoxin (MCMPCFTTDHQMARKCDDCCGGKGRGKCYGPQCLCR; SEQ ID NO:45) or a fragment thereof). In one embodiment, the toxin comprises LTCVKSNSIWFPTSEDCPDGQNLCFKRWQYISPRMYDFTRGCAATCPKAEY RDVINCCGTDKCNK (SEQ ID NO:46), MCMPCFTTDHQMARKCDDCCGGKGRGKCYGPQCLCR (SEQ ID NO:47), EDCIPKWKGCVNRHGDCCEGLECWKRRRSFEVCVPKTPKT (SEQ ID NO:48), LKCYQHGKVVTCHRDMKFCYHNTGMPFRNLKLILQGCSSSCSETENNKCC STDRCNK (SEQ ID NO:49), GTACSCGNSKGIYWFYRPSCPTDRGYTGSCRYFLGTCCTPAD (SEQ ID NO:50), ACSKKWEYCIVPILGFVYCCPGLICGPFVCV (SEQ ID NO:66), QNCCNGGCSSKWCRDHARCC (SEQ ID NO:51), ECRYWLGGCSAGQTCCKHLVCSRRHGWCVWDGTFS (SEQ ID NO:52), DDCLGMFSSCDPDNDKCCEGRKCNRKDKWCKYVL (SEQ ID NO:53), DCLGWFKGCDPDNDKCCEGYKCNRRDKWCKYKLW (SEQ ID NO:54), QPRRKLCILHRNPGRCYDKIPAFYYNQKKKQCERFDWSGCGGNSNRFKTIE ECRRTCIG (SEQ ID NO:55), QPLRKLCILHRNPGRCYQKIPAFYYNQKKKQCEGFTWSGCGGNSNRFKTIE ECRRTCIRK (SEQ ID NO:56), IKCTLSKDCYSPCKKETGCPRAKCINRNCKCYGCS (SEQ ID NO:57), LPPCCTPPKKHCPAPACKYKPCCKS (SEQ ID NO:58), VFINAKCRGSPECLPKCKEAIGKAAGKCMNGKCKCYP (SEQ ID NO:59), IVCHTTATSPISAVTCPPGENLCYRKMWCDVFCSSRGKVVELGCAATCPSK KPYEEVTCCSTDKCNPHPKQRPG (SEQ ID NO:60), IRDECCSNPACRVNNPHVC (SEQ ID NO:61), GCCSLPPCALSNPDYC, (SEQ ID NO:62) or GCCSDPRCAWRC (SEQ ID NO:63), or a fragment thereof having the activity, e.g., binding activity, of LTCVKSNSIWFPTSEDCPDGQNLCFKRWQYISPRMYDFTRGCAATCPKAEY RDVINCCGTDKCNK (SEQ ID NO:46), MCMPCFTTDHQMARKCDDCCGGKGRGKCYGPQCLCR (SEQ ID NO:47), EDCIPKWKGCVNRHGDCCEGLECWKRRRSFEVCVPKTPKT (SEQ ID NO:48), LKCYQHGKVVTCHRDMKFCYHNTGMPFRNLKLILQGC SSSCSETENNKCC STDRCNK (SEQ ID NO:49), GTACSCGNSKGIYWFYRPSCPTDRGYTGSCRYFLGTCCTPAD (SEQ ID NO:50), ACSKKWEYCIVPILGFVYCCPGLICGPFVCV,QNCCNGGCSSKWCRDHARC C (SEQ ID NO:51), ECRYWLGGCSAGQTCCKHLVCSRRHGWCVWDGTFS (SEQ ID NO:52), DDCLGMFSSCDPDNDKCCEGRKCNRKDKWCKYVL (SEQ ID NO:53), DCLGWFKGCDPDNDKCCEGYKCNRRDKWCKYKLW (SEQ ID NO:54), QPRRKLCILHRNPGRCYDKIPAFYYNQKKKQCERFDWSGCGGNSNRFKTIE ECRRTCIG (SEQ ID NO:55), QPLRKLCILHRNPGRCYQKIPAFYYNQKKKQCEGFTWSGCGGNSNRFKTIE ECRRTCIRK (SEQ ID NO:56), IKCTLSKDCYSPCKKETGCPRAKCINRNCK- CYGCS (SEQ ID NO:57), LPPCCTPPKKHCPA-PACKYKPCCKS (SEQ ID NO:58), VFINAKCRGSPE-CLPKCKEAIGKAAGKCMNGKCKCYP (SEQ ID NO:59), IVCHTTATSPISAVTCPPGENLCYRKMWCD-VFCSSRGKVVELGCAATCPSK KPYEEVTCC-STDKCNPHPKQRPG (SEQ ID NO:60), IRDECCSN-PACRVNNPHVC (SEQ ID NO:61), GCCSLPPCAL-SNPDYC, (SEQ ID NO:62) or GCCSDPRCAWRC (SEQ ID NO:63).

Figure 1:
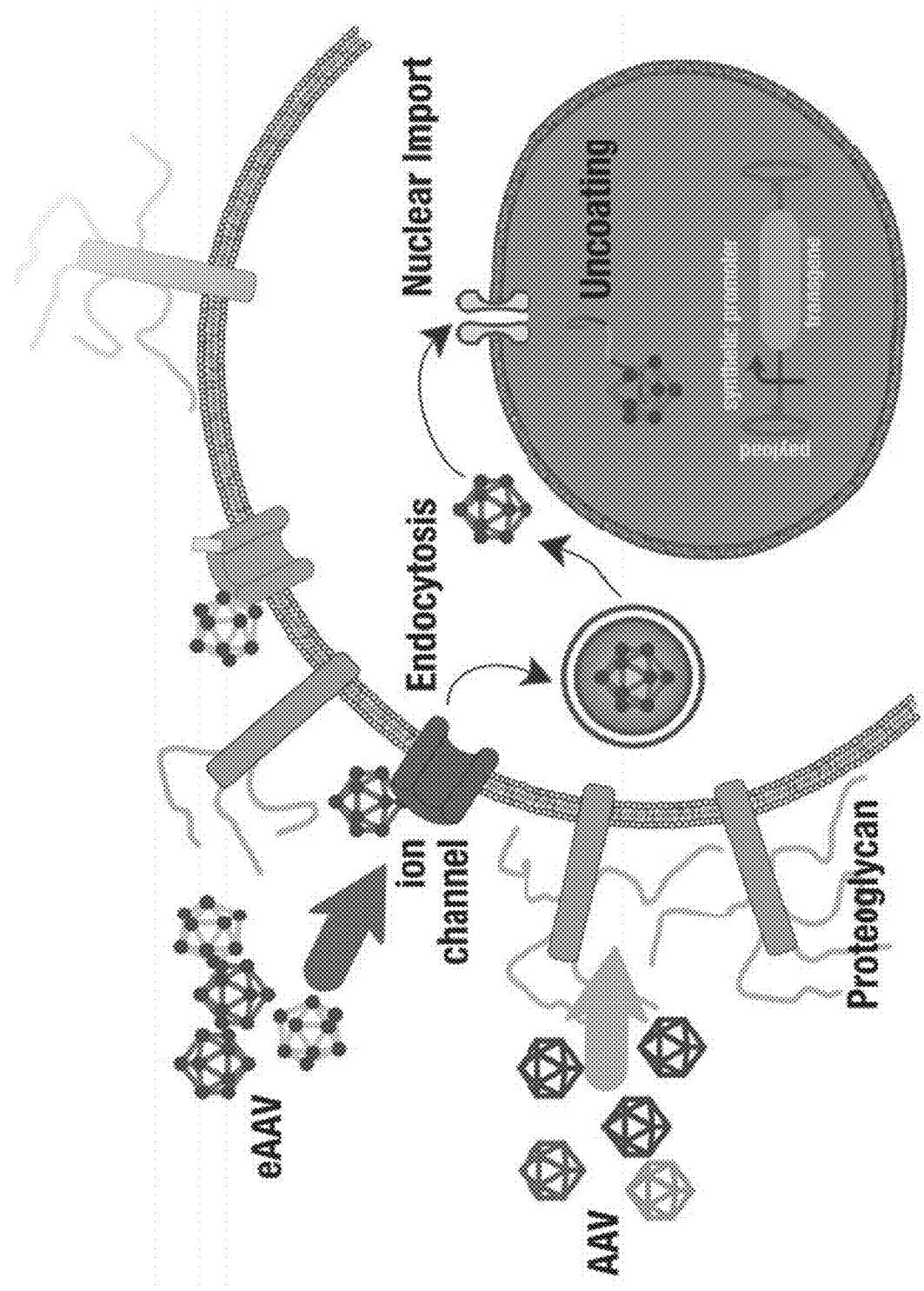
FIG. 1. Molecular Basis for Cell-type Specific Infection. Naturally occurring serotypes of AAV (wildtype AAV) have evolved to recognize ubiquitous surface receptors (e.g., proteoglycan). Engineered AAV (eAAV) are modified to not bind to such receptors and instead recognize ion channel expressed on specific cell type. Modifications introduced into eAAV must only redirect cell binding, and not interfere with virus particle endocytosis, endosome escape, nuclear import, uncoating, and release of the genetic material.
Figure 2:
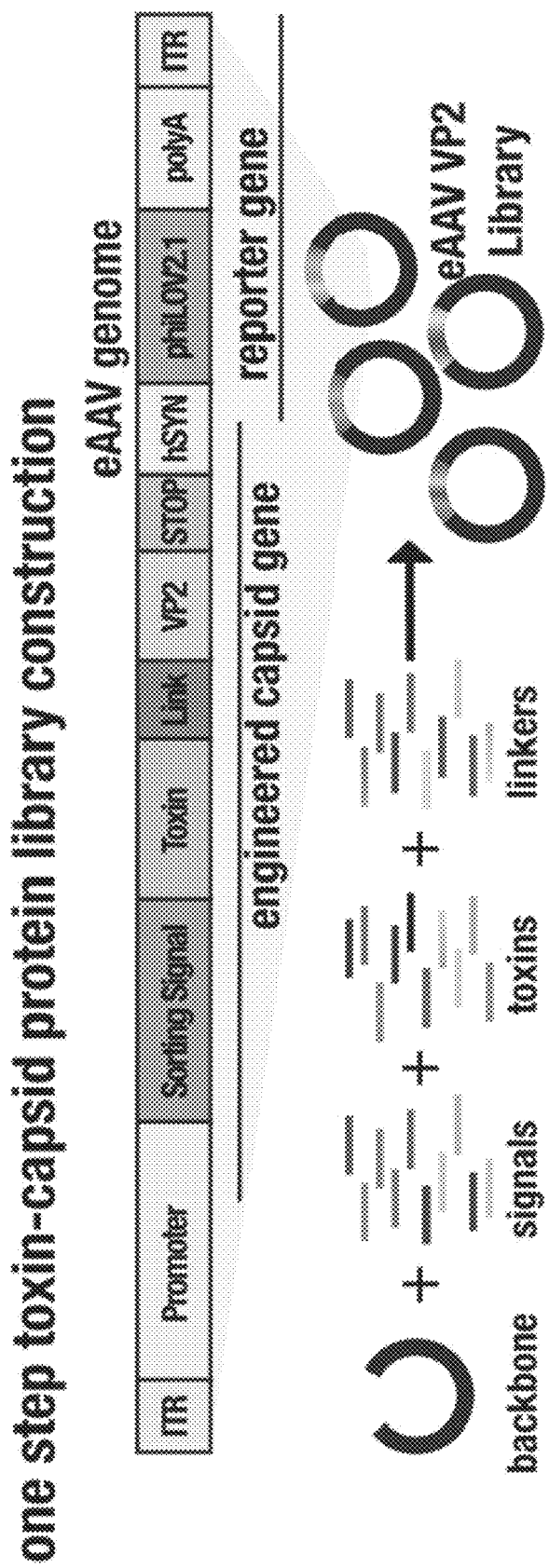
FIG. 2. Technology Foundation. One step library construction using Golden-Gate cloning of synthesized DNA fragments. The engineered capsid gene that endow eAAV with cell-type specificity encode a promoter (for recombinant virus production in AAV293 cells), sorting signal required for the peptide toxin to achieve their functional f coding sequence of interest in gene therapy (such as a gene encoding a protein of therapeutic or interest), a coding sequence of interest in vaccine development (such as a polynucleotide expressing a protein, polypeptide or peptide suitable for eliciting an immune response in a mammal), and/or a selectable or detectable marker.
Figure 3B:
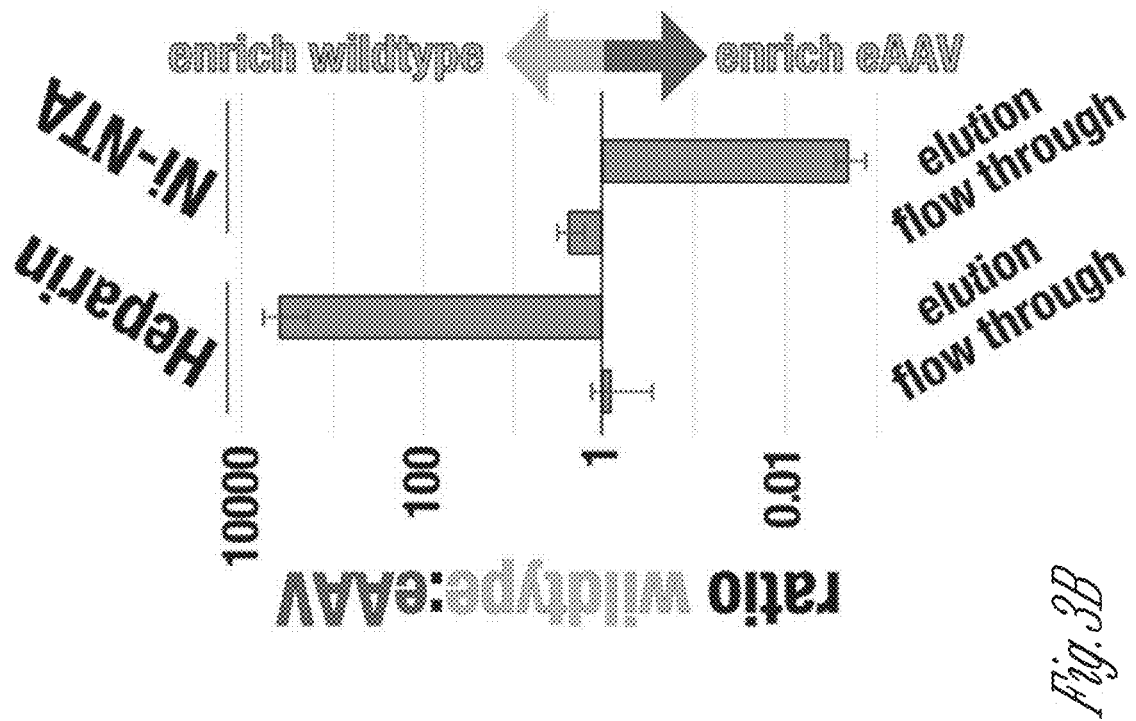
Figure 3A:
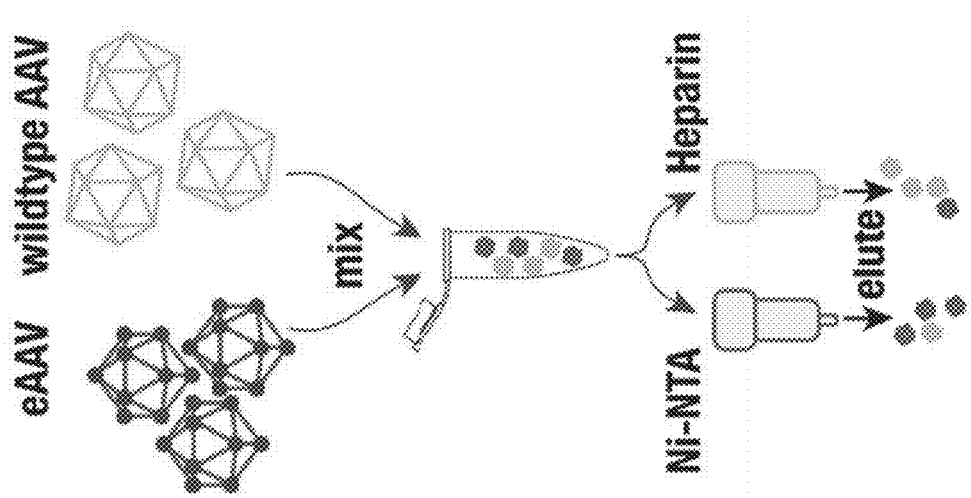

"AAV" is adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are many serotypes of primate AAVs, e.g., AAV-1 to AAV-10. For example, serotype AAV2 is used to refer to an AAV which contains capsid proteins encoded from the cap gene of AAV 2 and a genome containing 5' and 3' ITR sequences from the same AAV2 serotype. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector").

Tropism as used herein, is a term referring to the ability of a particular viral serotype to productively infect cells of differing phenotypes or organs to deliver their genomic information to the nucleus.

"Transduction" or "transducing" as used herein, are terms referring to a process for the introduction of an exogenous polynucleotide, e.g., a transgene in rAAV vector, into a host cell leading to expression of the polynucleotide, e.g., the transgene in the cell. The process includes one or more of 1) endocytosis of the chimeric virus, 2) escape from endosomes or other intracellular compartments in the cytosol of a cell, 3) trafficking of the viral particle or viral genome to the nucleus, 4) uncoating of the virus particles, and generation of expressible double stranded AAV genome forms, including circular intermediates. The rAAV expressible double stranded form may persist as a nuclear episome or optionally may integrate into the host genome. Methods used for the introduction of the exogenous polynucleotide include well-known techniques such as transfection, lipofection, viral infection, transformation, and electroporation, as well as non-viral gene delivery techniques. The introduced polynucleotide may be stably or transiently maintained in the host cell.

"Gene delivery" refers to the introduction of an exogenous polynucleotide into a cell for gene transfer, and may encompass targeting, binding, uptake, transport, localization, replicon integration and expression.

"Gene transfer" refers to the introduction of an exogenous polynucleotide into a cell which may encompass targeting, binding, uptake, transport, localization and replicon integration, but is distinct from and does not imply subsequent expression of the gene.

"Gene expression" or "expression" refers to the process of gene transcription, translation, and post-translational modification.

A "detectable marker gene" is a gene that allows cells carrying the gene to be specifically detected (e.g., distinguished from cells which do not carry the marker gene). A large variety of such marker genes are known in the art.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. A variety of positive and negative selectable markers are known in the art, some of which are described below.

An "rAAV vector" as used herein refers to an AAV vector comprising a polynucleotide sequence not of AAV origin (i.e., a polynucleotide heterologous to AAV), typically a sequence of interest for the genetic transformation of a cell. In preferred vector constructs of this invention, the heterologous polynucleotide is flanked by one or two AAV inverted terminal repeat sequences (ITRs). The term rAAV vector encompasses both rAAV vector particles and rAAV vector plasmids.

A "helper virus" for AAV refers to a virus that allows AAV (e.g., wild-type AAV) to be replicated and packaged by a mammalian cell. A variety of such helper viruses for AAV are known in the art, including adenoviruses, herpes viruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC.

An "infectious" virus or viral particle is one that comprises a polynucleotide component, which it is capable of delivering into a cell for which the viral species is trophic. The term does not necessarily imply any replication capacity of the virus.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "transcriptional regulatory sequence" or "TRS," as used herein, refers to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from that of the rest of the entity to which it is compared. For example, a polynucleotide introduced by genetic engineering techniques into a different cell type is a heterologous polynucleotide (and, when expressed, can encode a heterologous polypeptide). Similarly, a TRS or promoter that is removed from its native coding sequence and operably linked to a different coding sequence is a heterologous TRS or promoter.

"Packaging" as used herein refers to a series of subcellular events that results in the assembly and encapsidation of a viral vector. Thus, when a suitable vector is introduced into a packaging cell line under appropriate conditions, it can be assembled into a viral particle. Functions associated with packaging of viral vectors are described herein and in the art.

A "terminator" refers to a polynucleotide sequence that tends to diminish or prevent read-through transcription (i.e., it diminishes or prevent transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences," are specific sequences that tend to disrupt read-through transcription by RNA polymerase, presumably by causing the RNA polymerase molecule to stop and/or disengage from the DNA being transcribed. Typical examples of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-non-specific terminators or both. A variety of such terminator sequences are known in the art; and illustrative uses of such sequences within the context of the present invention are provided below.

"Host cells," "cell lines," "cell cultures," "packaging cell line" and other such terms denote higher eukaryotic cells, e.g., mammalian cells, such human cells, useful in the present invention. These cells can be used as recipients for recombinant vectors, viruses or other transfer polynucleotides, and include the progeny of the original cell that was transduced. It is understood that the progeny of a single cell may not necessarily be completely identical (in morphology or in genomic complement) to the original parent cell.

A "therapeutic gene," "prophylactic gene," "target polynucleotide," "transgene," "gene of interest" and the like generally refer to a gene or genes to be transferred using a vector. Typically, such genes are located within the rAAV vector (which vector is flanked by inverted terminal repeat (ITR) regions and thus can be replicated and encapsidated into rAAV particles). Target polynucleotides can be used in this invention to generate rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as E1A tumor suppressor genes or p53 tumor suppressor genes for the treatment of various cancers. To effect expression of the transgene in a recipient host cell, it is operably linked to a promoter, either its own or a heterologous promoter. A large number of suitable promoters are known in the art, the choice of which depends on the desired level of expression of the target polynucleotide; whether one wants constitutive expression, inducible expression, cell-specific or tissue-specific expression, etc. The rAAV vector may also contain a selectable marker.

A "gene" refers to a polynucleotide containing at least one open reading frame that is capable of encoding a particular protein after being transcribed and translated.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV ITR promoters, as well as heterologous promoters.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Genetic alteration" refers to a process wherein a genetic element is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. The genetic element may be introduced into a chromosome or mini-chromosome in the cell; but any alteration that changes the phenotype and/or genotype of the cell and its progeny is included in this term.

A cell is said to be "stably" altered, transduced or transformed with a genetic sequence if the sequence is available to perform its function during extended culture of the cell in vitro. In some examples, such a cell is "inheritably" altered in that a genetic alteration is introduced which is also inheritable by progeny of the altered cell.

The terms "polypeptide" and "protein" are used interchangeably herein to refer to polymers of amino acids of any length. The terms also encompass an amino acid polymer that has been modified; for example, disulfide bond formation, glycosylation, acetylation, phosphonylation, lipidation, or conjugation with a labeling component. Polypeptides such as "CFTR" and the like, when discussed in the context of gene therapy and compositions therefor, refer to the respective intact polypeptide, or any fragment or genetically engineered derivative thereof, that retains the desired biochemical function of the intact protein. Similarly, references to CFTR, and other such genes for use in gene therapy (typically referred to as "transgenes" to be delivered to a recipient cell), include polynucleotides encoding the intact polypeptide or any fragment or genetically engineered derivative possessing the desired biochemical function.

An "isolated" plasmid, virus, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture.

A preparation of AAV is said to be "substantially free" of helper virus if the ratio of infectious AAV particles to infectious helper virus particles is at least about $10^2$:1; e.g., at least about $10^4$:1, including at least about $10^6$:1 or at least about $10^8$:1. Preparations may also be free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

"Efficiency" when used in describing viral production, replication or packaging refers to useful properties of the method: in particular, the growth rate and the number of virus particles produced per cell. "High efficiency" production indicates production of at least 100 viral particles per cell; e.g., at least about 10,000 or at least about 100,000 particles per cell, over the course of the culture period specified.

An "individual" or "subject" treated in accordance with this invention refers to vertebrates, particularly members of a mammalian species, and includes but is not limited to domestic animals, sports animals, and primates, including humans.

"Treatment" of an individual or a cell is any type of intervention in an attempt to alter the natural course of the individual or cell at the time the treatment is initiated, e.g., eliciting a prophylactic, curative or other beneficial effect in the individual. For example, treatment of an individual may be undertaken to decrease or limit the pathology caused by any pathological condition, including (but not limited to) an inherited or induced genetic deficiency, infection by a viral, bacterial, or parasitic organism, a neoplastic or aplastic condition, or an immune system dysfunction such as autoimmunity or immunosuppression. Treatment includes (but is not limited to) administration of a composition, such as a pharmaceutical composition, and administration of compatible cells that have been treated with a composition. Treatment may be performed either prophylactically or therapeutically; that is, either prior or subsequent to the initiation of a pathologic event or contact with an etiologic agent.

The practice of the present invention will employ, unless otherwise indicated, conventional techniques of molecular biology, virology, microbiology, recombinant DNA, and immunology, which are within the skill of the art. Such techniques are explained fully in the literature.

rAAV Vectors

Besides prophylactic or therapeutic gene products, recombinant AAV vectors and/or viruses can also comprise polynucleotides that do not encode proteins, including, e.g., polynucleotides encoding for antisense mRNA (the complement of mRNA) which can be used to block the translation of normal mRNA by forming a duplex with it, and polynucleotides that encode ribozymes (RNA catalysts). In addition selected pairs of rAAV vectors having portions of open reading frames flanked by appropriately placed splice acceptor sites and/or splice donor sites, or having transcription regulatory sequences such as a heterologous enhancer, a heterologous promoter, or a heterologous enhancer and a promoter, may be employed. See, e.g., U.S. Pat. No. 6,436,392, the disclosure of which is incorporated by reference herein. For example, a first AAV vector may include a first DNA segment comprising a 5'-inverted terminal repeat of AAV; a second DNA segment comprising a promoter operably linked to a DNA fragment comprising an exon of a gene and a splice donor site, wherein the second DNA segment does not encode a full-length polypeptide; and a third DNA segment comprising a 3'-inverted terminal repeat of AAV; and a second AAV vector comprising linked: a first DNA segment comprising a 5'-inverted terminal repeat of AAV; a second DNA segment comprising a splice acceptor site and a DNA fragment with at least one other exon which together with the DNA segment of the first AAV vector encodes a full-length polypeptide; and a third DNA segment comprising a 3'-inverted terminal repeat of AAV. In one example, a first AAV vector includes the following: a first nucleic acid segment comprising a 5'-inverted terminal repeat of AAV; a second nucleic acid segment comprising a portion of a gene which includes a transcriptional regulatory region; a third nucleic acid segment comprising a splice donor site; and a fourth nucleic acid segment comprising a 3'-inverted terminal repeat of AAV; and a second AAV vector comprising linked: a first nucleic acid segment comprising a 5'-inverted terminal repeat of AAV; a second nucleic acid segment comprising a splice acceptor site; a third nucleic acid segment comprising a portion of a gene which together with the nucleic acid segment of the first AAV vector comprises a gene comprising an open reading frame which encodes a functional polypeptide; and a fourth nucleic acid segment comprising a 3'-inverted terminal repeat of AAV. In a further example, a first AAV vector includes the following: a first nucleic acid segment comprising a 5'-inverted terminal repeat of AAV; a second nucleic acid segment comprising a splice acceptor site; a third nucleic acid segment comprising a portion of a gene; and a fourth nucleic acid segment comprising a 3'-inverted terminal repeat of AAV; and a second composition comprising a second AAV vector comprising: a first nucleic acid segment comprising a 5'-inverted terminal repeat of AAV; a second nucleic acid segment comprising a portion of a gene which together with the nucleic acid segment above having the portion comprises a gene comprising an open reading frame which encodes a functional polypeptide, wherein the portion of the gene includes a transcriptional regulatory region; a third nucleic acid segment comprising a splice donor site; a fourth nucleic acid segment comprising a 3'-inverted terminal repeat of AAV; which vectors in a host cell yield a RNA transcript which comprises sequences from the first AAV vector linked to sequences from the second AAV vector, which sequences are positioned so that the splice donor site is 5' to the splice acceptor site, and which transcript is spliced to a mRNA which encodes the functional protein.

Adeno-associated viruses of any serotype are suitable to prepare rAAV, since the various serotypes are functionally and structurally related, even at the genetic level. All AAV serotypes apparently exhibit similar replication properties mediated by homologous rep genes; and all generally bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control. Among the various AAV serotypes, AAV2 is most commonly employed.

An AAV vector of the invention typically comprises a polynucleotide that is heterologous to AAV. The polynucleotide is typically of interest because of a capacity to provide a function to a target cell in the context of gene therapy, such as up- or down-regulation of the expression of a certain phenotype. Such a heterologous polynucleotide or "transgene," generally is of sufficient length to provide the desired function or encoding sequence.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and may be preferred when it is desired that the therapeutic or prophylactic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (mMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the heterologous polynucleotide generally comprises at least one coding region operatively linked to a suitable promoter, and may also comprise, for example, an operatively linked enhancer, ribosome binding site and poly-A signal. The heterologous polynucleotide may comprise one encoding region, or more than one encoding regions under the control of the same or different promoters. The entire unit, containing a combination of control elements and encoding region, is often referred to as an expression cassette.

The heterologous polynucleotide is integrated by recombinant techniques into or in place of the AAV genomic coding region (i.e., in place of the AAV rep and cap genes), but is generally flanked on either side by AAV inverted terminal repeat (ITR) regions. This means that an ITR appears both upstream and downstream from the coding sequence, either in direct juxtaposition, e.g., (although not necessarily) without any intervening sequence of AAV origin in order to reduce the likelihood of recombination that might regenerate a replication-competent AAV genome. However, a single ITR may be sufficient to carry out the functions normally associated with configurations comprising two ITRs (see, for example, WO 94/13788), and vector constructs with only one ITR can thus be employed in conjunction with the packaging and production methods of the present invention.

The native promoters for rep are self-regulating, and can limit the amount of AAV particles produced. The rep gene can also be operably linked to a heterologous promoter, whether rep is provided as part of the vector construct, or separately. Any heterologous promoter that is not strongly down-regulated by rep gene expression is suitable; but inducible promoters may be preferred because constitutive expression of the rep gene can have a negative impact on the host cell. A large variety of inducible promoters are known in the art; including, by way of illustration, heavy metal ion inducible promoters (such as metallothionein promoters); steroid hormone inducible promoters (such as the MMTV promoter or growth hormone promoters); and promoters such as those from T7 phage which are active in the presence of T7 RNA polymerase. One sub-class of inducible promoters are those that are induced by the helper virus that is used to complement the replication and packaging of the rAAV vector. A number of helper-virus-inducible promoters have also been described, including the adenovirus early gene promoter which is inducible by adenovirus E A protein; the adenovirus major late promoter; the herpesvirus promoter which is inducible by herpesvirus proteins such as VP16 or 1CP4; as well as vaccinia or poxvirus inducible promoters.

Methods for identifying and testing helper-virus-inducible promoters have been described (see, e.g., WO 96/17947). Thus, methods are known in the art to determine whether or not candidate promoters are helper-virus-inducible, and whether or not they will be useful in the generation of high efficiency packaging cells. Briefly, one such method involves replacing the p5 promoter of the AAV rep gene with the putative helper-virus-inducible promoter (either known in the art or identified using well-known techniques such as linkage to promoter-less "reporter" genes). The AAV rep-cap genes (with p5 replaced), e.g., linked to a positive selectable marker such as an antibiotic resistance gene, are then stably integrated into a suitable host cell (such as the HeLa or A549 cells exemplified below). Cells that are able to grow relatively well under selection conditions (e.g., in the presence of the antibiotic) are then tested for their ability to express the rep and cap genes upon addition of a helper virus. As an initial test for rep and/or cap expression, cells can be readily screened using immunofluorescence to detect Rep and/or Cap proteins. Confirmation of packaging capabilities and efficiencies can then be determined by functional tests for replication and packaging of incoming rAAV vectors. Using this methodology, a helper-virus-inducible promoter derived from the mouse metallothionein gene has been identified as a suitable replacement for the p5 promoter, and used for producing high titers of rAAV particles (as described in WO 96/17947).

Removal of one or more AAV genes is in any case desirable, to reduce the likelihood of generating replication-competent AAV ("RCA"). Accordingly, encoding or promoter sequences for rep, cap, or both, may be removed, since the functions provided by these genes can be provided in trans.

The resultant vector is referred to as being "defective" in these functions. In order to replicate and package the vector, the missing functions are complemented with a packaging gene, or a plurality thereof, which together encode the necessary functions for the various missing rep and/or cap gene products. The packaging genes or gene cassettes are in one embodiment not flanked by AAV ITRs and in one embodiment do not share any substantial homology with the rAAV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCA. Even further reductions in the frequency of generating RCA (e.g., by nonhomologous recombination) can be obtained by "splitting" the replication and encapsidation functions of AAV, as described by Allen et al., WO 98/27204).

The rAAV vector construct, and the complementary packaging gene constructs can be implemented in this invention in a number of different forms. Viral particles, plasmids, and stably transformed host cells can all be used to introduce such constructs into the packaging cell, either transiently or stably.

In certain embodiments, the AAV vector and complementary packaging gene(s), if any, are provided in the form of bacterial plasmids. AAV particles, or any combination thereof. In other embodiments, either the AAV vector sequence, the packaging gene(s), or both, are provided in the form of genetically altered (preferably inheritably altered) eukaryotic cells. The development of host cells inheritably altered to express the AAV vector sequence, AAV packaging genes, or both, provides an established source of the material that is expressed at a reliable level.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (as described in U.S. Pat. No. 5,658,776). Alternatively, a stable mammalian cell line with an AAV rep gene operably linked to a promoter can be used to supply replication functions (see, e.g., Trempe et al., WO 95/13392); Burstein et al. (WO 98/23018); and Johnson et al. (U.S. Pat. No. 5,656,785). The AAV cap gene, providing the encapsidation proteins as described above, can be provided together with an AAV rep gene or separately (see, e.g., the above-referenced applications and patents as well as Allen et al. (WO 98/27204). Other combinations are possible and included within the scope of this invention.

Uses of rAAV

The rAAV can be used for administration to an individual for purposes of gene therapy or vaccination. Suitable diseases for therapy include but are not limited to those induced by viral, bacterial, or parasitic infections, various malignancies and hyperproliferative conditions, autoimmune conditions, and congenital deficiencies. Gene therapy can be conducted to enhance the level of expression of a particular protein either within or secreted by the cell, e.g., suicide genes or immune system modulating genes. Vectors may be used to genetically alter cells either for gene marking, replacement of a missing or defective gene, or insertion of a therapeutic gene. Exemplary genes for delivery include but are not limited to Herpes simplex virus thymidine kinase (HSV-Tk) (converts prodrug Valacyclovir or ganciclovir into a toxic metabolite), CD (cytosine deaminase) (converts prodrug 5-fluorocytosine (5-FC) into a toxic metabolite, Varicella-Zoster virus thymidine kinase (VZV-tk) (converts prodrug 6-Methoxypurine arabinoside (ara-M) into a toxic metabolite), purine nucleoside phosphorylase (PNP) (onverts prodrug 6-Methylpurine-2-deoxyriboside into a toxic metabolite), nitroreductase (converts prodrug 5-Aziridinyl-2,4-dinitrobenzamide (CB 1954) into a toxic metabolite), beta-galatosidase (converts prodrugN-[4"-(beta-d-galacto-pyranosyl)-3"-nitrobenzyloxycarbonyl]daunomycin (Daun02) into a toxic metabolite), hepatic cytochrome P450-2B1 (converts prodrug Cyclophosphamide (CPA) and Ifosfamide (IFO) into a toxic metabolite), linamarase (converts prodrug Linamarin into a toxic metabolite), horseradish peroxidase (converts prodrug Horseradish Indole-3-acetic acid (IAA) and derivatives, or paracetamol into a toxic metabolite), carboxypeptidase A (converts prodrug Methotrexate (MTX)-α-peptide into a toxic metabolite), carboxypeptidase G2 (converts prodrug N,N-[(2-chloroethyl)(2-mesyloxy-ethyl) amino]benzoyl-1-glutamic acid (CMDA) into a toxic metabolite), IL-2, IL-4, interferon-gamma (gamma-IFN), tumor necrosis factor (TNF-alpha), M-CSF (macrophage colony-stimulating factor), or GM-CSF (granulocyte macrophage colony-stimulating factor).

Alternatively, a polynucleotide may be provided to the cell that decreases the level of expression. This may be used for the suppression of an undesirable phenotype, such as the product of a gene amplified or overexpressed during the course of a malignancy, or a gene introduced or overexpressed during the course of a microbial infection. Expression levels may be decreased by supplying a therapeutic or prophylactic polynucleotide comprising a sequence capable, for example, of forming a stable hybrid with either the target gene or RNA transcript (antisense therapy), capable of acting as a ribozyme to cleave the relevant mRNA or capable of acting as a decoy for a product of the target gene.

Vaccination can be conducted to protect cells from infection by infectious pathogens. As the traditional vaccine methods, vectors of this invention may be used to deliver transgenes encoding viral, bacterial, tumor or fungal antigen and their subsequent expression in host cells. The antigens, which expose to the immune system to evoke an immune response, can be in the form of virus-like particle vaccines or subunit vaccines of virus-coding proteins. Alternatively, as the method of passive immunotolerization, vectors of this invention might be used to deliver genes encoding neutralizing antibodies and their subsequent expression in host non-hematopoietic tissues. The vaccine-like protection against pathogen infection can be conducted through direct provision of neutralizing antibody from vector-mediated transgene expression, bypassing the reliance on the natural immune system for mounting desired humoral immune responses.

The introduction of the rAAV vectors may involve use of any number of delivery techniques (both surgical and non-surgical) which are available and well known in the art. Such delivery techniques, for example, include vascular catheterization, cannulization, injection, inhalation, endotracheal, subcutaneous, inunction, topical, oral, percutaneous, intra-arterial, intravenous, and/or intraperitoneal administrations. Vectors can also be introduced by way of bioprostheses, including, by way of illustration, vascular grafts (PTFE and dacron), heart valves, intravascular stents, intravascular paving as well as other non-vascular prostheses. General techniques regarding delivery, frequency, composition and dosage ranges of vector solutions are within the skill of the art.

In particular, for delivery of a vector of the invention to a tissue, any physical or biological method that will introduce the vector to a host animal can be employed. Vector means both a bare recombinant vector and vector DNA packaged into viral coat proteins, as is well known for administration. Simply dissolving a rAAV vector in phosphate buffered saline has been demonstrated to be sufficient to provide a vehicle useful for muscle tissue expression, and there are no known restrictions on the carriers or other components that can be coadministered with the vector (although compositions that degrade DNA should be avoided in the normal manner with vectors). Pharmaceutical compositions can be prepared as injectable formulations or as topical formulations. rAAVs may also be delivered to the central nervous system via intravenous, intrathecal or intracerebroventricular delivery, e.g., using foam. Numerous formulations for both intramuscular injection and transdermal transport have been previously developed and can be used in the practice of the invention. The vectors can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the chimeric or rHBoV vector as a free acid (DNA contains acidic phosphate groups) or a pharmacologically acceptable salt can be prepared in water suitably mixed with a surfactant such as hydroxypropylcellulose. A dispersion of viral particles can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the rAAV vector in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the methods of preparation include but are not limited to vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for incorporation into a transdermal patch, and can include known carriers, such as pharmaceutical grade dimethylsulfoxide (DMSO).

Compositions of this invention may be used in vivo as well as ex vivo. In vivo gene therapy comprises administering the vectors of this invention directly to a subject. Pharmaceutical compositions can be supplied as liquid solutions or suspensions, as emulsions, as foams (liquid mixed in gas) or as solid forms suitable for dissolution or suspension in liquid prior to use. Typically, the viral vectors are in a pharmaceutically suitable pyrogen-free buffer such as Ringer's balanced salt solution (pH 7.4). Although not required, pharmaceutical compositions may optionally be supplied in unit dosage form suitable for administration of a precise amount.

An effective amount of virus is administered, depending on the objectives of treatment. An effective amount may be given in single or divided doses. Where a low percentage of transduction can cure a genetic deficiency, then the objective of treatment is generally to meet or exceed this level of transduction. In some instances, this level of transduction can be achieved by transduction of only about 1 to 5% of the target cells, but is more typically 20% of the cells of the desired tissue type, usually at least about 50%, at least about 80%, at least about 95%, or at least about 99% of the cells of the desired tissue type. As a guide, the number of vector particles present in a single dose given by transcranial endoscopy will generally be at least about $1\times10^{12}$, e.g., about $1\times10^{13}$, $1\times10^{14}$, $1\times10^{15}$ or $1\times10^{16}$ particles, including both DNAse-resistant and DNAse-susceptible particles. In terms of DNAse-resistant particles, the dose will generally be between $1\times10^{12}$ and $1\times10^{16}$ particles, more generally between about $1\times10^{12}$ and $1\times10^{15}$ particles. The treatment can be repeated as often as every two or three weeks, as required, although treatment once in 180 days may be sufficient.

To confirm the presence of the desired DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence of a polypeptide expressed from a gene present in the vector, e.g., by immunological means (immunoprecipitations, immunoaffinity columns, ELISAs and Western blots) or by any other assay useful to identify the presence and/or expression of a particular nucleic acid molecule falling within the scope of the invention.

To detect and quantitate RNA produced from introduced DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the DNA segment in question, they do not provide information as to whether the DNA segment is being expressed. Expression may be evaluated by specifically identifying the polypeptide products of the introduced DNA sequences or evaluating the phenotypic changes brought about by the expression of the introduced DNA segment in the host cell.

Thus, the effectiveness of the genetic alteration can be monitored by several criteria, including analysis of physiological fluid samples, e.g., urine, plasma, serum, blood, cerebrospinal fluid or nasal or lung washes. Samples removed by biopsy or surgical excision may be analyzed by in situ hybridization, PCR amplification using vector-specific probes, RNAse protection, immunohistology, or immunofluorescent cell counting. When the vector is administered by bronchoscopy, lung function tests may be performed, and bronchial lavage may be assessed for the presence of inflammatory cytokines. The treated subject may also be monitored for clinical features, and to determine whether the cells express the function intended to be conveyed by the therapeutic or prophylactic polynucleotide.

The decision of whether to use in vivo or ex vivo therapy, and the selection of a particular composition, dose, and route of administration will depend on a number of different factors, including but not limited to features of the condition and the subject being treated. The assessment of such features and the design of an appropriate therapeutic or prophylactic regimen is ultimately the responsibility of the prescribing physician.

The foregoing description provides, inter alia, methods for generating high titer preparations of recombinant viruses that are substantially free of helper virus (e.g., adenovirus) and cellular proteins. It is understood that variations may be applied to these methods by those of skill in this art without departing from the spirit of this invention.

Exemplary Use

The modification of AAV capsids allows for safer and more precise gene therapies. AAV has shown to be safe (including non-human primate brain), able to infect both dividing and arrested cells, however their broad tropism makes targeting hard, and means that high virus titer are required (since most virus is sequestered by tissue/cells not meant to be targeted). Potentially, any disorder, whose pathology is characterized by a specific surface receptor expression profile to which we can find a high affinity binder (e.g., peptide toxin), would become targetable with precision.

One specific application is that of (brain) cancer gene therapy. There is a great need: Brain cancer is the leading cause of cancer-related deaths in children and adults under 35. Current treatment approaches, predominantly surgery and chemotherapy, are not well adapted to unique properties of this cancer, as evidenced by low 5-year survival rates (17%) and poor prognosis (15 months). Gene therapy, while promising in preclinical testing, has so far not been effective in clinical trials.

Importantly, many brain cancers exhibit distinct profiles of ion channels and receptors, often related to cancer pathology. For example, the most invasive gliomas overexpress chloride channels that mediate cancer invasivness. Peptide toxins targeting these chloride channels have in fact been used in clinical trials (later abandoned) for radiotherapy, and have been shown to bind cancer with high specificity.

Surgical resection is the most common primary treatment for brain cancer. Unfortunately, in many cases secondary tumors appear within centimeters from the original resection site, stemming from highly invasive glioma cells that have escaped the solid tumor mass (and thus resection). Naturally, the surgeon has to balance extent of resection and potential impact on brain function. Thus, an oncolytic AAV product that is formulated as a foam or an emulsion, and is applied by the surgeon after resection of the main tumor mass, may have efficacy. Its role is to seek out the remaining (escaped) glioma cells by virtue of cancer-cell tropism and small (highly diffusive) size of viral capsid, and to kill these cells by delivering a 'cellular suicide' gene. A corollary, the unique access provided by the surgery circumvent many of the issue encountered with systemically delivered AAV gene therapy. These included broad neutralizing serum responses and limited ability to cross the blood-brain barrier.

Exemplary targets and corresponding toxins are shown below.

| Target | Peptide Toxin (Voltage Sensor Toxin*) |
|---|---|
| ASIC1/3 | PcTx1, MITx, Mambalgin-3, Mambalgin-1, APETx2 |
| Nav1.2 | μ-CNTX-Pn1a* |
| Nav1.8 | μO-CNTX MrVIB, μ-CNTX SIIIA, ProTx-I, Pterinotoxin-1, VSTX3 |
| Cav2.2 | ω-CNTX MVIIA |
| Kv1.1 | DTX-K |
| Kv1.2 | αDTX, DTX-I, Hemitoxin, Charybdotoxin, κ-CNTX RIIIJ, TsTXK-α |

-continued

| Target | Peptide Toxin (Voltage Sensor Toxin*) |
|---|---|
| Kv2.1 | GxTx*, HaTx*, VSTx1* |
| Shaker Kv | CONK1, |
| α6 nAChR | α-CNTX PIA |
| α7 nAChR | α-BGTx, α-CNTX GID, α-CNTX PnIB, α-CNTX IMI, SLURP-1 |
| α3/β4 nAChR | α-BGTx |

The invention will be further described by the following non-limiting examples.

Example 1

Materials and Methods
Identify Peptide Toxins, Linkers and Sorting Signals to be Encoded The amino acid sequence for peptide toxin, that targets the desired cell-surface receptors, if available, is retrieved from databases, such a Conoserver (http://conoserver.org), Arachnoserver (http://www.arachnoserver.org) (Queensland Facility for Advanced Bioinformatics, Australia), the Animal Toxin Database (protchem.hunnu.edu.cn/toxin/) (Hunan Normal University, ChangSha, China), the Bioactive Peptide Database (K.U. Leuven, Belgium), and for integrated data including target channels, the UniProtKB/Swiss-Prot Tox-Prot program (http://www.uniprot.org/program/Toxins). Amino acid sequences are reverse translated assuming mammalian codon usage tables.

The amino acid sequence for linkers are rationally designed to achieve different biophysical properties (length, hydrophobicity, propensity to form secondary structure), and reverse translated assuming mammalian codon usage tables.

The amino acid sequence for sorting signals are derived from literature searches that reported previously used protein export signals (e.g. Schmidt et al., 2014; Ibanez-Tallon et al., 2004), and from databases (e.g. www.signalpeptide.de, more than 19,000 mammalian and viral sorting signals). Amino acids sequences are reverse translated assuming mammalian codon usage tables.

Generation of Plasmids

BP-00142 was generated from pAAV-DJ (Cellbiolabs) by mutating residues 585-588 (cap numbering) to a HA tag (amino acid sequence YPYDVPDYA), in addition to mutating the alternative start codon for splice form 2 of the cap gene (VP2)—T138A.

BP-00171 was generated from pGolden-AAV (Addgene Plasmid #51424) by replacing basepairs 200 to 671, flanked by Noti sites, with a gene cassette that contains in linear order: two outward facing type IIS restriction sites (BsaI), splice form 2 of the cap gene (VP2) in which residues 585-588 have been replaced by a hexahistidine tag (6×HIS), a SV40 polyadenylation signal, the human synapsin promoter region (hSYN), the fluorescent protein phiLOV2.1 (Christie et al., 2012), a truncated Woodchuck Hepatitis Virus Posttranscriptional Regulatory Element (WPRE3), and a synthetic polyadenylation signal.

Donor plasmids were generated by custom gene synthesis (Genscript and Gen9) for 23 sorting signals (see Table 1), 85 peptide toxins (see Table 2), 22 peptide linkers (see Table 3), and two (2) promoters (see Table 4).

TABLE 1

Sorting Signals

| Identifier (see FIG. 4) | Source Protein | Amino Acid Sequence |
|---|---|---|
| S01 | Ig_heavy | MGWSCIILFLVATATGAHS (SEQ ID NO: 1) |
| S02 | GRIN1 | MSTMRLLTLALLFSCSVA (SEQ ID NO: 2) |
| S03 | NR1 | MSTMHLLTFALLFSCSFARA (SEQ ID NO: 3) |
| S04 | GluR1 | MQHIFAFFCTGFLGAVVG (SEQ ID NO: 4) |
| S05 | NR2B | MKPSAECCSPKFWLVLAVLAVSGSKA (SEQ ID NO: 5) |
| S06 | Tryp | MSALLILALVGAAVA (SEQ ID NO: 6) |
| S07 | STIM1 | MDVCVRLALWLLWGLLLHQGQS (SEQ ID NO: 7) |
| S08 | dBIP | MKLCILLAVVAFVGLSLG (SEQ ID NO: 8) |
| S09 | hBIP | MKLSLVAAMLLLLSAARA (SEQ ID NO: 9) |
| S10 | Calreticulin | MLLSVPLLLGLLGLAVA (SEQ ID NO: 10) |
| S11 | GluR2 | MQKIMHISVLLSPVLWGLIFGVSS (SEQ ID NO: 11) |
| S12 | Hemagglutinin | MKTIIALSYIFCLVFA (SEQ ID NO: 12) |
| S13 | ACHA7(human) | MRCSPGGVWLALAASLLHVSLQ (SEQ ID NO: 13) |
| S14 | hGH | MATGSRTSLLLAFGLLCLPWLQEGSA (SEQ ID NO: 14) |
| S15 | Prolactin | MDSKGSSQKGSRLLLLLVVSNLLLCQGVVS (SEQ ID NO: 15) |
| S16 | CD47 | MWPLVAALLLGSACCGSA (SEQ ID NO: 16) |
| S17 | Lamp2 | MVCFRLFPVPGSGLVLVCLVLGAVRSYA (SEQ ID NO: 17) |
| S18 | Transferrin | MRLAVGALLVCAVLGLCLA (SEQ ID NO: 18) |
| S19 | ACHB4 | MRGTPLLLVVSLFSLLQD (SEQ ID NO: 19) |
| S20 | ACHA7(rat) | MGLRALMLWLLAAAGLVRESLQG (SEQ ID NO: 20) |
| S21 | ChR2 | MDYGGALSAVGRELL (SEQ ID NO: 21) |
| S22 | Notch1 | MPPLLAPLLCLALLPALA (SEQ ID NO: 22) |
| S23 | MHC | MGAMAPRTLLLLLAAALAPTQRA (SEQ ID NO: 23) |

TABLE 2

Peptide Toxins

| Identifier | Amino Acid Sequence |
|---|---|
| PcTx1 (*) | EDCIPKWKGCVNRHGDCCEGLECWKRRRSF EVCVPKTPKT (SEQ ID NO: 48) |
| Mambalgin-1 (*) | LKCYQHGKVVTCHRDMKFCYHNTGMPFRNL KLILQGCSSSCSETENNKCCSTDRCNK (SEQ ID NO: 49) |
| APETx2 (*) | GTACSCGNSKGIYWFYRPSCPTDRGYTGSC RYFLGTCCTPAD (SEQ ID NO: 50) |
| μO-CNTX MrVIB | ACSKKWEYCIVPILGFVYCCPGLICGPFVC V (SEQ ID NO: 66) |
| μ-CNTX SIIIA | QNCCNGGCSSKWCRDHARCC (SEQ ID NO: 51) |
| ProTx-I | ECRYWLGGCSAGQTCCKHLVCSRRHGWCVW DGTFS (SEQ ID NO: 52) |
| Pterinotoxin-1 | DDCLGMFSSCDPDNDKCCEGRKCNRKDKWC KYVL (SEQ ID NO: 53) |
| VSTX3 | DCLGWFKGCDPDNDKCCEGYKCNRRDKWCK YKLW (SEQ ID NO: 54) |
| αDTX (*) | QPRRKLCILHRNPGRCYDKIPAFYYNQKKK QCERFDWSGCGGNSNRFKTIEECRRTCIG (SEQ ID NO: 55) |
| DTX-I (*) | QPLRKLCILHRNPGRCYQKIPAFYYNQKKK QCEGFTWSGCGGNSNRFKTIEECRRTCIRK (SEQ ID NO: 56) |
| Hemitoxin (*) | IKCTLSKDCYSPCKKETGCPRAKCINRNCK CYGCS (SEQ ID NO: 57) |
| κ-CNTX RIIIJ (*) | LPPCCTPPKKHCPAPACKYKPCCKS (SEQ ID NO: 58) |
| TsTX-K-α (*) | VFINAKCRGSPECLPKCKEAIGKAAGKCMN GKCKCYP (SEQ ID NO: 59) |
| α-BGTx(V31 iso) (*) | IVCHTTATSPISAVTCPPGENLCYRKMWCD VFCSSRGKVVELGCAATCPSKKPYEEVTCC STDKCNPHPKQRPG (SEQ ID NO: 60) |
| α-CNTX GID (*) | IRDECCSNPACRVNNPHVC (SEQ ID NO: 61) |
| α-CNTX PnIB (*) | GCCSLPPCALSNPDYC (SEQ ID NO: 62) |
| α-CNTX IMI (*) | GCCSDPRCAWRC (SEQ ID NO: 63) |

TABLE 3

Peptide Linkers

Figure 4B:
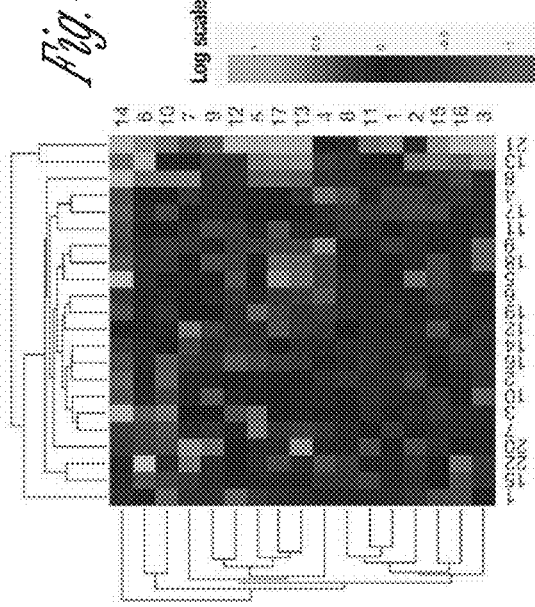
Figure 4D:
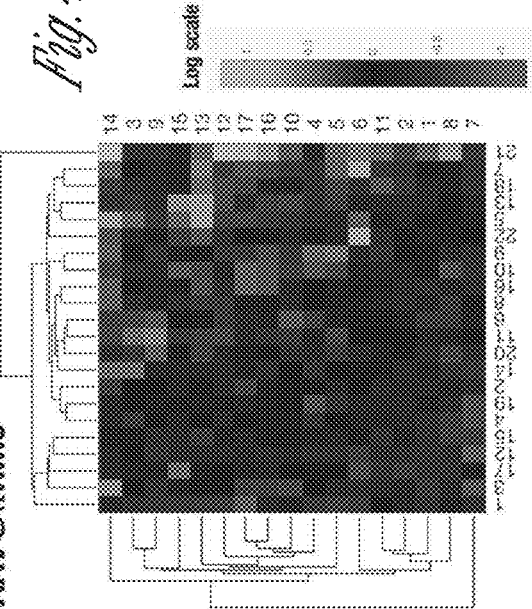
Figure 4A:
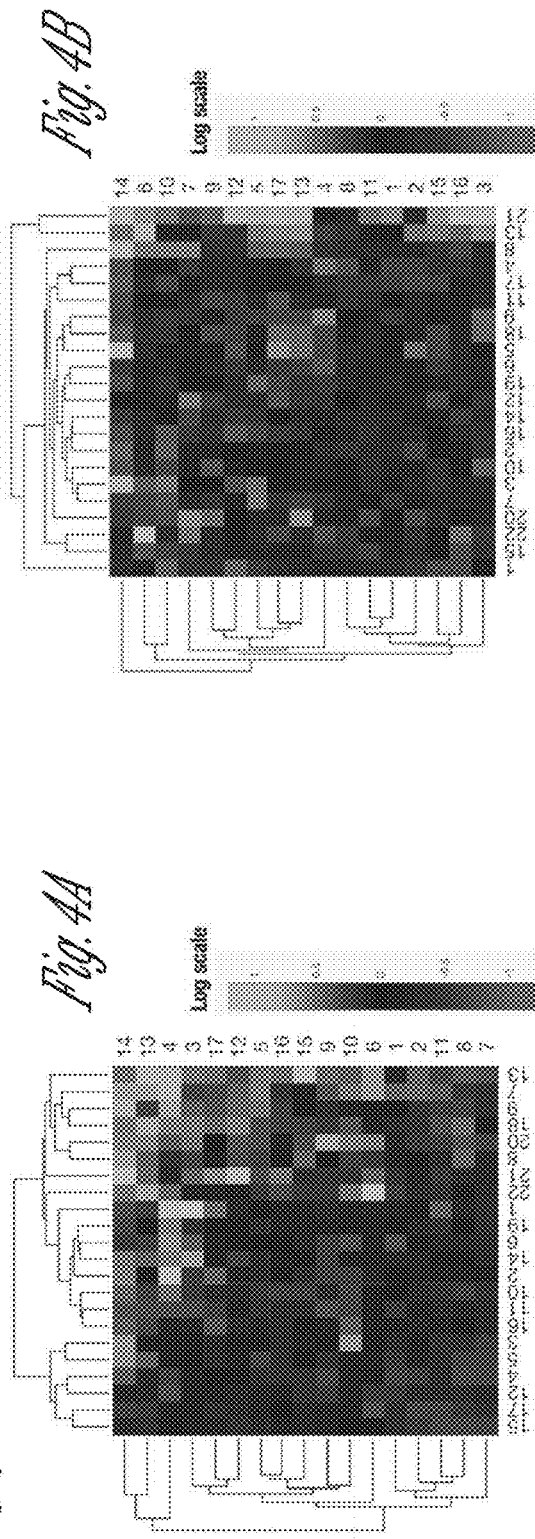
Figure 4C:
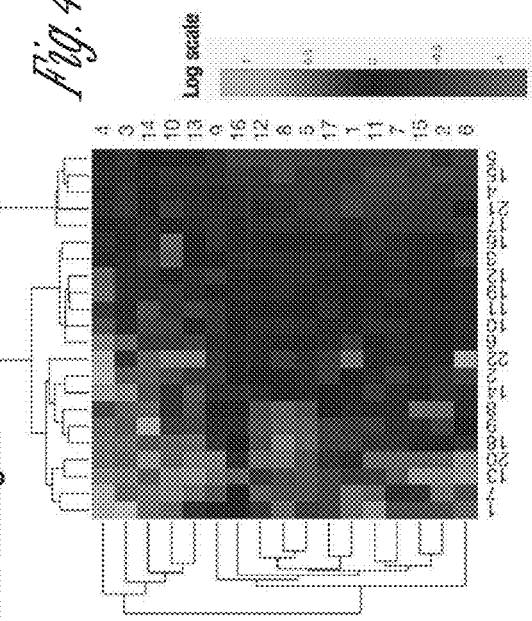
Figure 6:
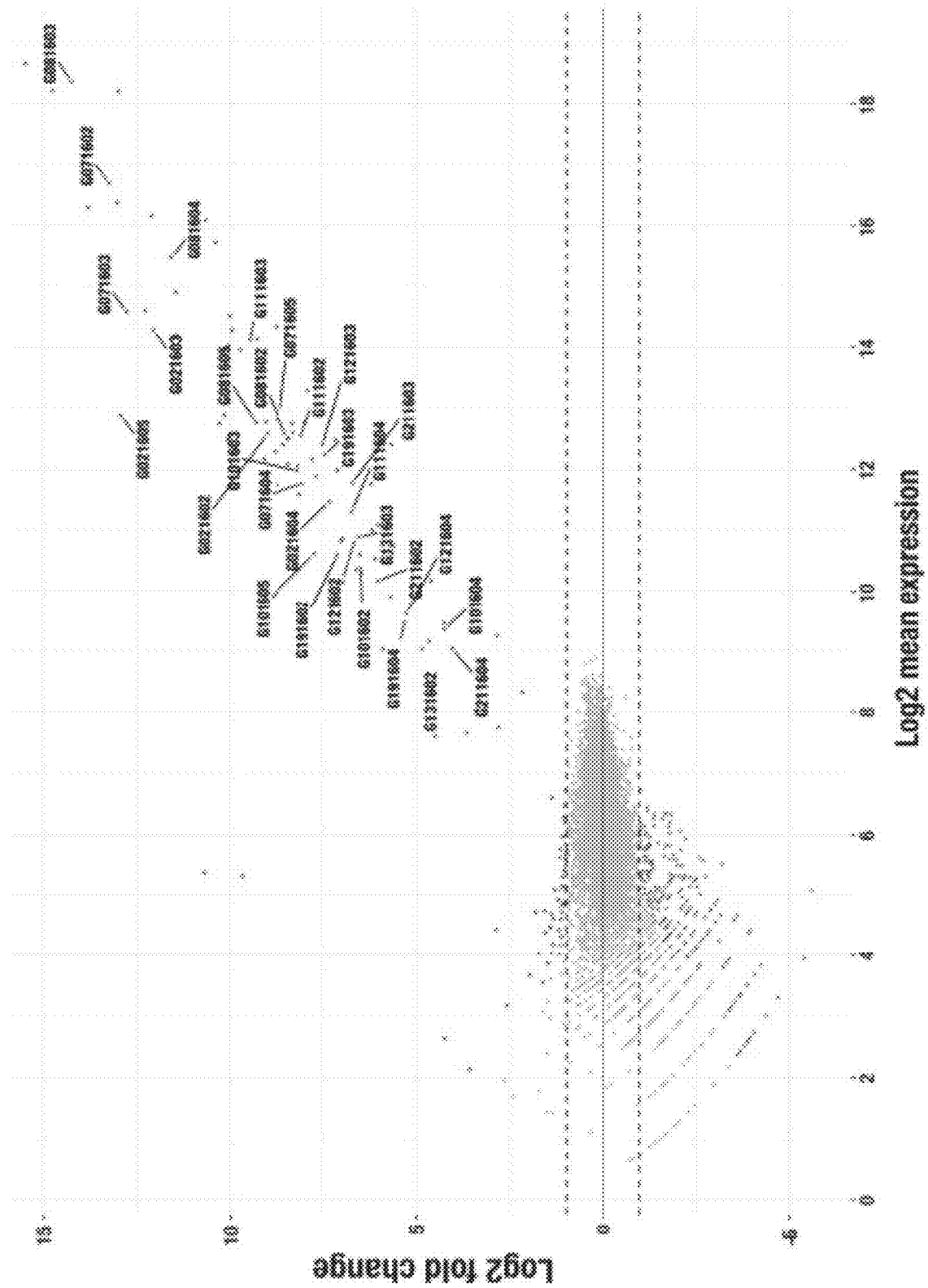
Figure 8A:
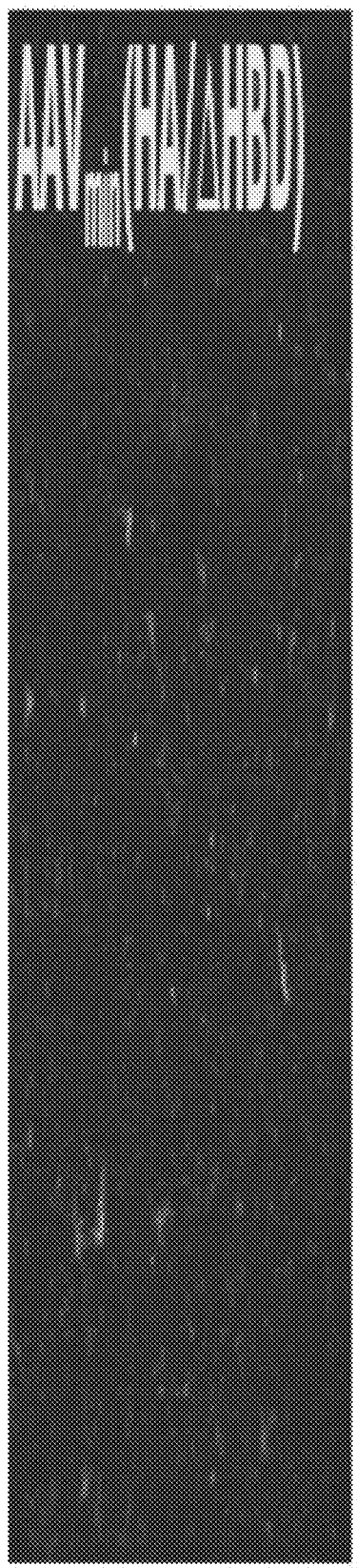
Figure 8B:
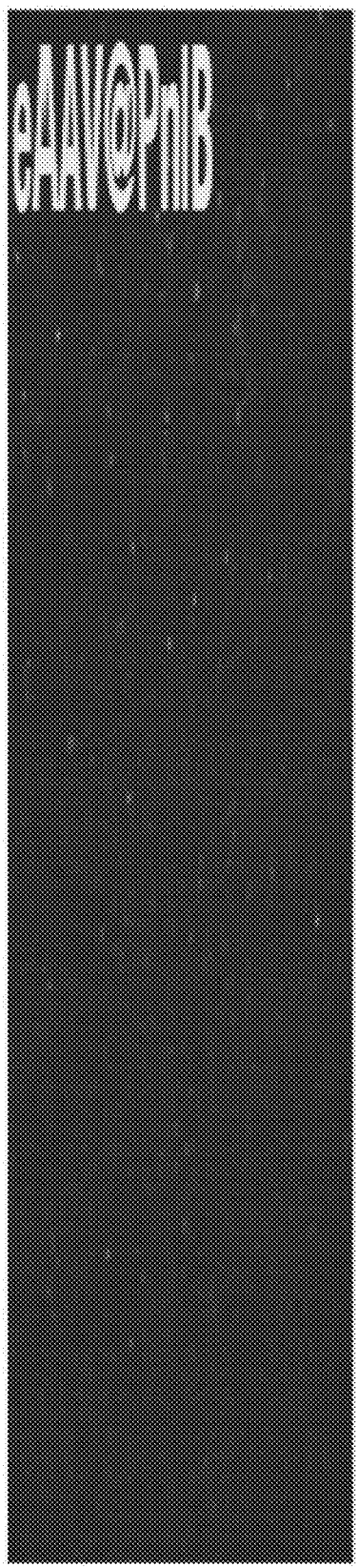
Figure 8C:
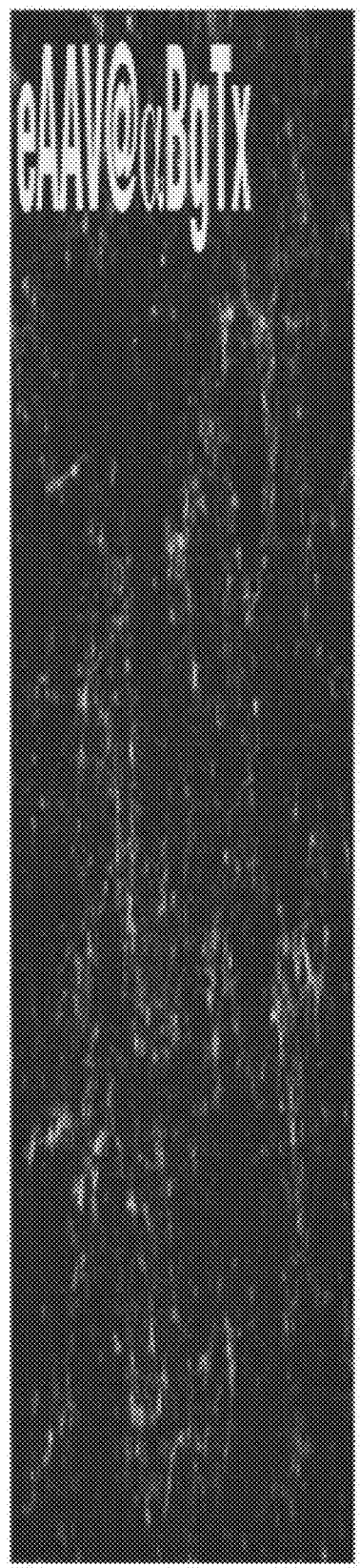
Figure 9A:
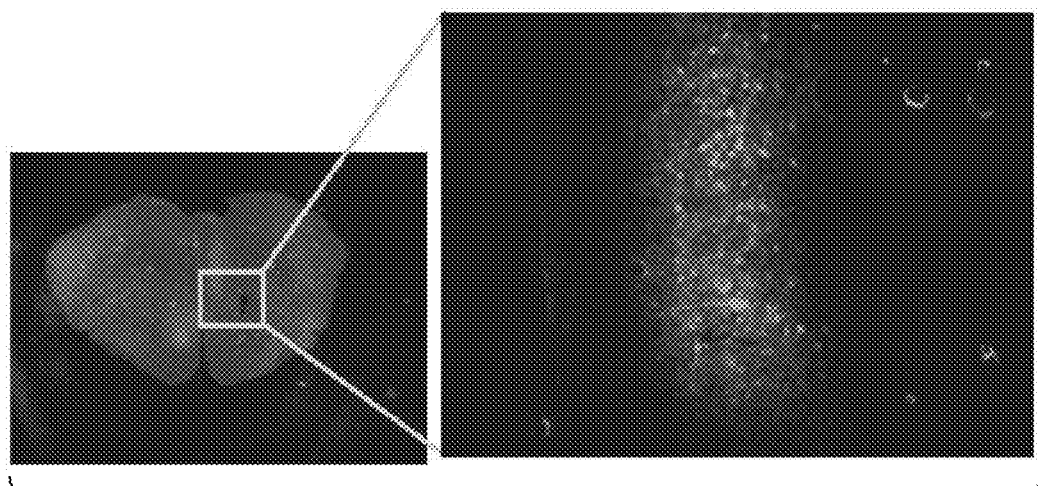
Figure 9B:
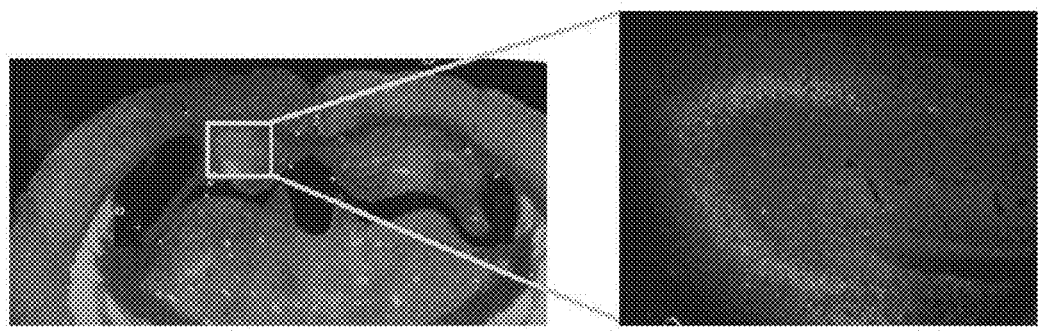
Figure 9C:
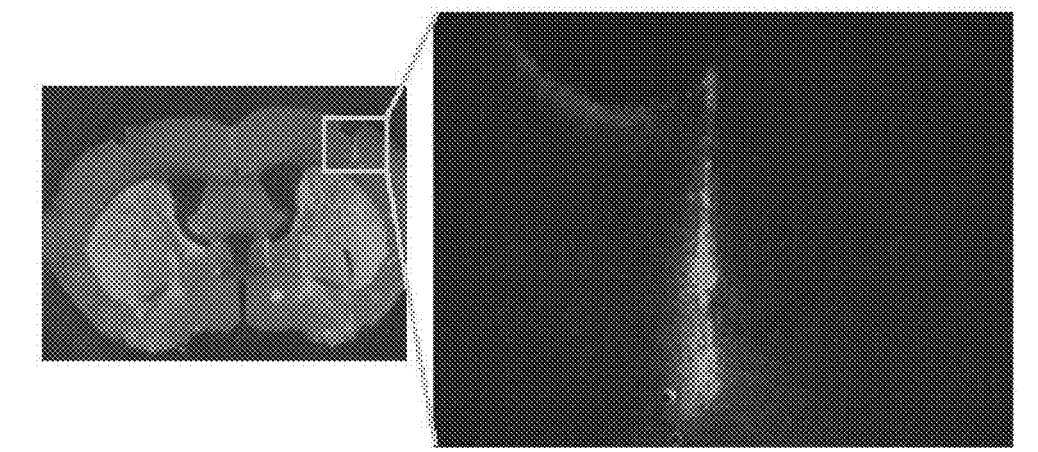

| Identifier (see FIG. 4) | Amino Acid Sequence |
|---|---|
| L01 | GSA (SEQ ID NO: 24) |
| L02 | GSAGSAG (SEQ ID NO: 25) |
| L03 | GSAGSAGSAG (SEQ ID NO: 26) |
| L04 | GSAGSAGSAGGSAGSAGSAG (SEQ ID NO: 27) |
| L05 | AAADYKDDDDKIDAAAGGALCN (SEQ ID NO: 28) |
| L06 | IDYKDDDDKLAAAGNGNGNGNGNGNGDGNGGAL CN (SEQ ID NO: 29) |
| L07 | PPPPPPPPPPPPPPPP (SEQ ID NO: 30) |
| L08 | GNGN (SEQ ID NO: 31) |
| L09 | GNGNAGNGN (SEQ ID NO: 32) |
| L10 | GNGNAGNGNAGNGNAGNGN (SEQ ID NO: 33) |
| L11 | AEAAAKA (SEQ ID NO: 34) |
| L12 | AEAAAKEAAAKA (SEQ ID NO: 35) |
| L13 | AEAAAKEAAAKEAAAKA (SEQ ID NO: 36) |
| L14 | AEAAAKEAAAKEAAAKEAAAKA (SEQ ID NO: 37) |
| L15 | PDANLRPEDLW (SEQ ID NO: 38) |
| L16 | PDANLRPEDLWANHSKVV (SEQ ID NO: 39) |
| L17 | PDANLRPEDLWANHSKVVPLPKPPHMKDSA (SEQ ID NO: 40) |
| L18 | EEEEKKKQQEEEAERLRRIQEEMEKERKRREEDEK RRRKEEEERRMKLEMEAKRKQEEEERKKREDDEKR KKK (SEQ ID NO: 41) |
| L19 | EEEEKKKEEEEKKQKEEQERLAKEEAERKQEEQE RLERERKEREEQEKKAKEEAERIAKLEAEKKAEEE RKAKEEEERKAKEEEERKKKEEQERLAKEKEEAER KAAEEKKAKEEQERKEKEEAERKQR (SEQ ID NO: 42) |
| L20 | EEEEKKKEEEEKKQKEEQERLAKEEAERKQEEQE RLAKEEAERKQKEEEERKQKEEEERKQKEEEERKL KEEQERKAAEEKKAKEEAERKAKEEQERKAEEERK KKEEEERLERERKEREEQEKKAKEEAERIAKLEAE KKAEEERKAKEEEERKAEEEERKKKEEQERLAKE KEEAERKAAEEKKAKEEEERKKKEEQERKEKEEAERKQR (SEQ ID NO: 43) |

TABLE 4

Promoters

| Identifier | DNA Sequence |
|---|---|
| SV40 | Gtgtgtcagttagggtgtggaaagtccccaggct ccccagcaggcagaagtatgcaaagcatgcatct caattagtcagcaaccaggtgtggaaagtcccca ggctccccagcaggcagaagtatgcaaagcatgc atctcaattagtcagcaaccatagtcccgcccct aactccgcccatcccgcccctaactccgcccagt tccgcccattctccgcccccatggctgactaattt ttttatttatgcagaggccgaggccgcctcggc ctctgagctattccagaagtagtgaggaggcttt tttggagCCTAGGCTTTTGCAAA (SEQ ID NO: 64) |
| CMV | Gacattgattattgactagttattaatagtaatc aattacggggtcattagttcatagcccatatatg gagttccgcgttacataacttacggtaaatggcc cgcctggctgaccgcccaacgacccccgcccatt gacgtcaataatgacgtatgttcccatagtaacg ccaatagggactttccattgacgtcaatgggtgg agtatttacggtaaactgcccacttggcagtaca tcaagtgtatcatatgccaagtacgccccctatt |

TABLE 4-continued

| Promoters | |
|---|---|
| Identifier | DNA Sequence |
| | gacgtcaatgacggtaaatggcccgcctggcatt atgcccagtacatgaccttatgggactttcctac ttggcagtacatctacgtattagtcatcgctatt accatggtgatgcggttttggcagtacatcaatg ggcgtggatagcggtttgactcacggggatttcc aagtctccaccccattgacgtcaatgggagtttg ttttggcaccaaaatcaacgggactttccaaaat gtcgtaacaactccgccccattgacgcaaatggg cggtaggcgtgtacggtgggaggtctatataagc agagct (SEQ ID NO: 65) |

In one embodiment, the chimeric VP2 has one of the following linkers: L3, L4, L12, L13, L14, or L17. In one embodiment, the chimeric VP2 encoded by the vector has one of the following sorting signals: S7, S13, S18, S20, or S21. In one embodiment, the chimeric VP2 has one of APETx, PxTx1, Mambalgin1, αDTX, DTX-I, TsTX-K-α, K-CNTX RIIIJ, Hemitoxin, α-CNTX PnIB, α-CNTX GID, α-CNTX ImL αBgTx (V31 isoform). In one embodiment, the chimeric VP2 has one of Mambalgin, κ-CNTX RIIU, Hemitoxin, or αBgTx (V31 isoform).

VP-toxin fusion production libraries (e.g. BP-00171@toxin01) were constructed through Golden Gate cloning (Engler et al., 2009) by mixing BP-00171 with one toxin-encoding plasmid with equimolar amounts of all sorting signal plasmids, all peptide linker plasmids, and all promoters plasmid in a restriction/ligation reaction. In other words, the toxin was held constant and plasmid libraries were constructed in which every other component is randomly selected. The total expected diversity for each library is 1,012 (2 promoters×23 sorting signals X 22 linkers).

Helper-Free Production of AAV

Viral particles were produced following establish procedures (Greiger et al., 2008). Briefly, to produce HBD knockout virus, $AAV_{min}$(HA/ΔHDB), equimolar amounts (3 μg total) of pHelper (Cellbiolabs), BP-00142, and pAAV-CAG-GFP (Addgene Plasmid #37825) were transfected into AAV293 cells (Cellbiolabs) using Polyethyleneimine (Polysciences). To produce peptide-toxin displaying virus (nomemclature: eAAV@toxin) equimolar amounts (3 μg total) of pHelper (Cellbiolabs), BP-00142, BP-00171 containing the desired toxin-VP2 library were transfected into AAV293 cells (Cellbiolabs) using Polyethyleneimine. To produce wildtype virus (i.e., virus particles with functional HBD domains that do not display peptide toxins), equimolar amounts (3 μg total) of pAAV-DJ (Cellbiolabs), pAAV-CAG-GFP, and pHelper were transfected into AAV293 cells using Polyethyleneimine.

Cells ($0.1\times10^6$ cells) were plated in 24-well plates and maintained in D10 (DMEM, 10% fetal bovine serum (FBS), Penicillin/Streptomycin, Sodium Pyruvate (all Life Technologies). 48 hours after transfection, cells were washed twice with DMEM, the scraped off the culture dish, spun down and flash frozen in liquid nitrogen. Viral particles were liberated from the cells by three freeze-thaw cycles. Cell debris was spun down and supernatant, containing the majority of viral particles (knockout virus, eAAV or wildtype AAV), was stored at 4 deg C. until further use.

Affinity Purification of eAAV Displaying Peptide Toxin

To assess whether any peptide toxin can be displayed on the viral capsid surface, we use a biochemical enrichment assay. Equal volumes of eAAV and wildtype AAV supernatants were mixed, followed by division into two parts. One part was poured over a HiTRAP Heparin (Life Technologies) affinity purification column-binding viral particle that contain HBD domains, i.e. wildtype AAV-equilibrated with RB1 (20 mM Tris-HCl pH 8.0, 150 mM NaCl). The other part was poured over a HiTRAP HisCrude (Life Technologies) affinity purification column-binding viral particle that display peptide toxins, i.e. eAAV-equilibrated with RB2 (20 mM Tris-HCl pH 8.0, 150 mM NaCl, 20 mM imidazole). Both columns were wash with 5 column volumes using RB1+200 mM NaCl or RB2+40 mM imidazole, respectively. Viral particles were eluted using RB1+500 mM NaCl or RB2+500 mM imidazole, respectively.

For large scale purification of eAAV, supernatants from helper-free production were, without mixing with wildtype virus supernatants, were incubated with Ni-NTA-modified Dynabeads (Life Technologies) equilibrated in RB2. Beads were washed three times with RB2+40 mM imidazole, and eluted using RB2+500 mM imidazole.

All eluted fractions were concentrated by ultrafiltration using an Amicon Ultra-4 (100K) centrifuge filter. To liberate viral genome, each sample (containing 1× DNAse I buffer) was incubated at 37 deg C. for 30 minutes with DNAse I (1 unit, NEB) to digest viral genome that are not encapsulated by the proteinous viral capsid shell, followed by heat-inactivation of the DNAse at 65 deg C. for 20 minutes. To each sample Proteinase K buffer (1×, 10 mM, Tris-HCl, 8.0, 1 mM EDTA, 1% SDS) was added, as well as 0.8 units of Proteinase K (NEB). Incubation at 37 deg C. for 60 minutes, followed by heat denaturation at 95 deg C. for 10 minutes liberated viral genomes from viral capsids. Single-stranded viral genome DNA was purified using Clean & Concentrator 5 columns (Zymo research), and eluted with water.

Determination of Virus Titer by qPCR

To determine relative ratios of wildtype:eAAV viral particles in eluted and concentration samples, we determined viral titers by qPCR. Quantitative PCR on the viral genomes was performed at the UMN Genomics Center using LightCycler 480 SybrGreen I Master (Roche) and primers (IDT DNA) that are specific to shared viral genome features of wildtype and eAAV, as well as specific features, such as encoding GFP (wildtype) or phiLOV2.1 (eAAV). Viral genome titers (expressed as [DNAse I resistant capsids]/ul) were calculated using the crossing point method in comparison to a standard curve generated from pAAV-CAG-GFP and BP-00171 plasmids.

Determine which Peptide Toxins are Compatible with Virus Display by Illumina MiSEQ To determine which combinations of promoters, sorting signals, peptide toxins, and peptide linkers are compatible with display on AAV viral capsid, we created amplicon libraries from toxin plasmid libraries before helper-free virus production, and on liberated viral genomes after 6×HIS-tag affinity purification. Amplicon libraries were subjected to paired-end (2×300) Illumina sequencing at the UMN Genomics Center. Raw sequencing results were filtered for read quality (MSI Galaxy), and mapped against references toxin-VP2 assemblies via custom Matlab scripts. Relative enrichment/depletion ratios for each promoters, sorting signals, peptide toxins, and peptide linkers combination were calculated as $\log_{10}(N_{before}/N_{after})$.

Cell Culture (Primary Hippocampal Neurons)

All procedures involving animals were in accordance with the National Institute of Health Guide for the care and use of laboratory animals and approved by the University of Minnesota Animal Care and Use Committee. Hippocampal regions from CD-1 IGSm mice (Charles River Laboratories) postnatal day 0-1 were isolated and digested with papain (100 units in Hanks balanced salt solution supplemented with 35 mM glucose, 1 mM Kynurenic acid, 0.3 mg/ml L-Cysteine and 10 mM $MgCl_2$) for 6-8 minutes. The reaction was stopped by washing and addition of 10 mg/ml bovine serum albumin and 10 mg/ml ovomucoid inhibitor (Worthington). The tissue was then mechanically dissociated by triturating through P1000 plastic pipette tips, and settled by gravitation. Dissociated neurons in the supernatant were plated on Matrigel-coated glass coverslip (BD Bioscience) and maintained in plating medium (MEM, 10% fetal bovine serum, 0.5% glucose, 10 mM HEPES, 2 mM L-glutamine, 0.5 mg/ml holo-transferrin, 25 µg/mL insulin, B27 supplement, buffered to pH 7.4 with NaOH.

Infection Assay (Neuron)

Neurons were infected at 2 days in vitro with eAAV viral particles. Plating media was removed and saved for later use. Neurons were washed twice with pre-warmed MEM. Viral particles, diluted in MEM, were added at the desired multiplicity of infection to the neurons. Neurons were then incubated for 1 hour allowing with viral particles, before 1 ml of conditioned plating media was added back. The next day another 1 ml of plating media containing Cytosine 13-D-arabinofuranoside (Sigma) to inhibit glia growth.

After 14 days in vitro, fluorescent protein reporter expression was quantified by microscopy and compared to negative control (neurons infected with HDB-knockout virus, $AAV_{min}$(HA/ΔHDB).

Experiments

To redirect AAV tropism towards specific ion channels and receptors by genetically fusing peptide toxins to viral capsid proteins, the following rationale was applied. AAVs are non-enveloped ssDNA viruses that can infect both dividing and non-dividing cells. They are maintained in the mammalian host cell, enabling long-term expression. AAVs encapsulate a 4.7 kb genome encoding two viral genes, rep and cap, give rise to multiple gene products through alternative splicing and read-through translation. Most of the rep products are involved in genome replication and packaging, while the cap gene encodes three capsid proteins VP1, VP2, and VP3. 60 copies of these beta-barrel proteins at a ratio of 1:1:18 form an icosahedral virus shell. VP1 and VP3 is important for viral particle infectivity and capsid stability; VP2 is a redundant and nonessential protein (Warrington et al., 2004). Recombinant AAV can be produced in vitro by using helper virus-free systems that provide the necessary adenovirus gene products required for transactivation of viral promoters and splicing from helper plasmids and stable cell lines (Greiger et al., 2014).

The approach builds on previously developed systems that allow the independent expression of three AAV capsid proteins, VP1, VP2, and VP3 (Hagen et al., 2014). Providing wild-type VP1 and VP3 in trans enables the insertion of large protein domains, for example peptide toxins (~5 kDa) at the N-terminus of VP2 without—we hypothesized—affecting packaging and infectivity.

The majority of receptors that AAV binds to prior to endocytosis are proteoglycans via a heparin binding domain (HBD) present on all three splice forms of viral capsid protein (FIG. 1). As we describe below, our first step was to knock out endogenous tropism by introducing mutation in the HBD domain. We designed a DNA construct encoding the AAV2 rep and cap genes (VP-1/3) with point mutations at the VP2 start codon (T138A) and in the HDB domain (ΔHBD), so only VP1 and VP3 would be expressed. We could successfully package this minimal AAV from mutated VP1 & VP3 alone, as tested by DNAseI protection assay and qPCR (data not shown). Nevertheless, these minimal viral particles were not able to infect neurons (FIG. 5), so this non-infectious recombinant AAV system was the stepping stone for introducing toxin-VP2 fusion proteins into AAV to redirect binding of viral particles to channel and receptor on the surface of neurons.

To make rapid progress, a preprotrypsin signal peptide, the snake venom peptide toxin αDTX, and 17 protein linkers—together all smaller than 7 kDa—were combined into a toxin-VP2 fusion protein library, which we hypothesized can route through the ER to the nucleus, and can functionally incorporate into the viral capsid (FIG. 2). As in the case of VP1 and VP3, this toxin-VP2 fusion protein carries a 6×HIS tag insertion at position 587 (VP1 numbering), which interferes with binding of VP2 to heparan sulfate (ΔHBD) and allows us to purify virus particle using Ni-NTA resins. When these two constructs—one encoding toxin-VP2 (with 6×HIS, ΔHBD), the other VP1 & VP3 (HA, ΔHBD), are cotransfected into AAV293 cells together with a third plasmid containing E2A, E4, and VA RNA genes from adenovirus (pHelper), we can produce engineered recombinant AAV (eAAV) in vitro. Having produced recombinant eAAV, by enriching VP2 containing viral particles with magnetic Ni-NTA beads it could be directly test if the toxin-VP2 fusion had successfully incorporated into the presumed eAAV capsid. Only VP2 contains the 6×HIS tag and thus only particles that co-assembled VP2 with VP1 and VP3 are pulled down. If viral capsids are composed of VP1/3 only—because toxin-VP2 fusion didn't fold, traffic, or is structurally incompatible with capsid assembly-viral particles will not be enriched with 6×HIS-tag purification.

This enrichment assay was used to obtain direct experimental evidence that toxin-VP2 fusion indeed can incorporate into eAAV particles (FIG. 3). One experiment with wildtype (i.e. containing HDB domains) VP1 & VP3 packaged a viral genome encoding GFP ("green"). The second experiment with VP1 (HA, ΔHBD), VP3(HA, ΔHBD), toxin-VP2(6×HIS, ΔHBD) packaged a viral genome encoding mKate2 ("red"). After freeze/thawing to liberate viral particles from the producer cells, we mixed both supernatants thus creating a specific starting ratio of green:red which we normalize to 1. Then this mixed supernatant containing both wildtype AAV and eAAV particles was equally divided. One part was subjected to Heparin column affinity purification, the other to Ni-NTA affinity purification. The Heparin column should only enrich wildtype AAV (i.e., ratio green:red increases, >>1), since eAAV has all HBD domains mutated. Conversely, the Ni-NTA column should only enrich eAAV (i.e., ratio green:red decreases, <<1), since these are the only viral particles that contain 6×HIS tags (in toxin-VP2). The relative ratio of wild-type virus and eAAV can be followed at each step by subjecting samples to DNAseI treatment (this degrades unencapsulated viral genomes), followed by release of capsid-protected viral genomes with Proteinase-K, detergent, and heat denaturation. Genome copies are then counted by qPCR. Several independent runs have confirmed that Heparin affinity column only enrich wildtype virus, and that Ni-NTA column only enrich eAAVs (FIG. 3). When using Heparin columns, eAAV particles are depleted about 4000-fold from the elution; when using Ni-NTA columns eAAV particles are enriched ~800-fold since they contain 6×HIS on the αDTX-VP2 fusion protein. Control experiments with wild-type (AAV-DJ) virus resulted in the expected inverse enrichment/depletion pattern. In other words, that αDTX-VP2 fusion can incorporate into eAAV particles.

To gain more general insight into which combinations of sorting signals, peptide linkers, and peptide toxins are compatible with viral display, eAAV production libraries were constructed for several different peptide toxins (annotated with an asterisk in Table 2) targeting three types of ion channels (ASIC1/3 cation channels, Kv1.x voltage-dependent K+ channels, and nicotinic acetylcholine receptors, nAChR). After producing recombinant eAAV, viral particles that bind to Ni-NTA dynabeads, implying that these viral particles display folded peptide toxins that carry the 6×HIS tag, were purified. Then the viral genomes contained in the eluted fraction of viral particles, reasoning that these contain the genes that went into producing the displayed-functional-toxin-VP2 protein, were liberated. In other words, since the enriched virus particles themselves contain the genetic information that supported their functional production genotype/phenotype linkage is maintained. The enriched viral genomes, as well as the production plasmid libraries (e.g., BP-00171@toxin01), were subjected to MiSEQ illumina sequencing. Illumina sequencing not only tells what sorting signals, linkers, and toxin are found together on functionally eAAVs, it also gives quantitative information, e.g., how many times a specific combination is encountered. By comparing the abundance of a specific combination before eAAV production and after eAAV enrichment, sorting signals and linkers that are more likely to result in functional eAAV, for a given peptide toxins context, can be deduced. FIG. 4 illustrates the outcome of this comparison for 5 representative examples (3 shown plus average of all 5 peptide toxins). Certain sorting signals (e.g., derived from ac7 nAChR) may be universally better than others to produce eAAVs. Similarly, alpha-helical linkers that are longer than 5 amino acids and have a high propensity to form alpha helices are likely better than short or bulky linkers.

Finally, to assess whether eAAV can infect neurons—implying that s only targeting of viral particles was changed and did not interfere with the remaining life cycles and gene delivery-eAAVs were constructed with 12 peptide toxins targeting ASIC1/3, Kv1.x and nAChR, using sorting signals and linkers that in the previous experiment performed well (22 amino acids alpha helical linker, a7 nAChR signal). After producing recombinant virus, cleared freeze/thaw supernatants were used to infect cultured hippocampal neurons at day 2 in vitro. Neurons were imaged after 14 days in vitro and phiLOV2.1 expression, which indicates infection of neurons and gene delivery, quantified. phiLOV2.1 expression in eAAV infected neurons was compared to that achieved with $AAV_{min}$(HA/ΔHBD) (FIG. 5). This knockout AAV is expected to be non-infectious as all HBD domains are mutated to a HA tag. Indeed, only spurious reporter gene expression was observed. For eAAVs tested on the other hand, while some clearly did not successfully infect neurons (e.g. eAAV@αPnIB), several of them did with great efficiency (e.g. eAAV@αBgTx). Importantly, a specific peptide toxin could be identified for each channel class, thus providing further evidence that eAAV can be engineered for arbitrary receptor targets.

Together, the experiments demonstrate that 1) endogenous tropism and infectivity of naturally occurring AAV can be knocked-out by introducing point mutation into capsid protein HBD domains, 2) rationally chosen peptide toxins can be fused to virus capsid protein, and integrate these synthetic fusion proteins into assembled viral capsid, and 3) channel- and receptor-specific peptide toxins that are displayed on the virus surface restores infectivity in a peptide toxin specific- and presumably receptor specific fashion, such that arbitrary transgenes can be delivered to user-selectable classes of cell types.

In one embodiment, the chimeric VP2 has one of the following linkers: L3, L4, L12, L13, L14, or L17. In one embodiment, the chimeric VP2 encoded by the vector has one of the following secretion signals: S7, S13, S18, S20, or S21. In one embodiment, the chimeric VP2 has one of APETx, PxTx1, Mambalgin1, αDTX, DTX-I, TsTX-K-α, κ-CNTX RIIIJ, Hemitoxin, α-CNTX PnIB, α-CNTX GID, α-CNTX ImI, αBgTx (V31 isoform). In one embodiment, the chimeric VP2 has one of Mambalgin1, κ-CNTX RHIIIJ, Hemitoxin, or αBgTx (V31 isoform).

Example 2

One goal is to redirect AAV tropism towards specific ion channels and receptors by genetically fusing peptide toxins to viral capsid proteins.

Recombinant AAV can be produced in vitro by using helper virus-free systems that adenovirus gene products for transactivation of viral promoters and splicing from helper plasmids and stable cell lines. The approach includes, in one embodiment, a system that allows the independent expression of three AAV capsid proteins, VP1, VP2, and VP3. Providing wild-type VP1 and VP3 in trans allows for the insertion of large protein domains, for example, peptide toxins (e.g., having a size of about 5 kDa) at the N-terminus of VP2 without potentially affecting packaging and infectivity.

Diverse promoters, trafficking signals, protein linkers, and peptide toxins were designed and assembled into libraries of toxin-VP2 fusion proteins. Specifically, 22 secretion signals were screened for their ability to forward 17 different peptide toxins fused through 21 different linkers to VP2 from the ER, where the peptide toxin acquires its fold, to the nucleus, where the toxin-VP2 fusion protein is incorporated into the viral capsid. The assay involved transfecting the corresponding library (about 8000 members total) into HEK293FT together with plasmid delivering the packaged transgene, VP1/VP3(DHBD), and helper genes. As in the case of VP1 and VP3, this toxin-VP2 fusion protein carries mutations (for VP2: 6×HIS tag), which interferes with binding of VP2 to heparan sulfate (DHBD) and allows purification of virus particle using Ni-NTA resins. The toxin-VP2 plasmid furthermore encodes a fluorescent marker (phiLOV2.1) to allow subsequent assay in neurons, and because it is flanked by two AAV2 ITR, it becomes packaged into the viral particles. This allows maintenance of genotype/phenotype linkage; a toxin-VP2 fusion that enables virus packaging itself becomes packaged in the virus. When these two constructs, one encoding toxin-VP2 (with 6×HIS, DHBD) and the other encoding VP1 & VP3 (DHBD), are cotransfected into HEK293FTcells together with a plasmid containing E2A, E4, and VA RNA genes from adenovirus (pHelper), engineered recombinant AAV (eAAV) are produced in vitro.

Plasmids were introduced into HEK293 cells in amounts that minimize multiple (different) toxin-VP2 fusion plasmids transfected into the same cell which could result in disrupting the genotype/phenotype linkage and add noise to the selection screen. Sequencing (see below) indicated that the assay has good signal to noise properties, and that cross-packaging is not an issue.

After producing eAAV libraries in HEK293 cells (in triplicate), packaged viral particles were isolated through repeated freeze thawing. Viral particles that displayed peptide toxin were enriched using Ni-NTA conjugated magnetic beads by virtue of the 6×HIS tag that is introduced into the toxin-VP2 fusion. After thorough nuclease digestion to remove carryover plasmid DNA, viral genomes were liberated from particle by heat and Proteinase K. Multiple displacement amplifications (MDA) were used to both convert genomic DNA into dsDNA and to amplify the enriched eAAV variant genes that are encoded as part of the purified viral genome. Unlike PCR, MDA is unbiased and therefore less likely to produce amplification artifacts that could bias downstream analysis.

Samples from amplified enriched genomes, infection controls, and input plasmid libraries were sequenced (MiSeq). By comparing the distribution of read for a specific eAAV variant (Signal X+Toxin Y+Linker Z, etc.), before and after enrichment, it can be inferred which components produce toxin-containing viral particles. To simplify the analysis and to ensure rigor, the before and after samples were treated as a differential gene expression problem (with each eAAV variant being treated as gene). This allowed use of analysis workflow, e.g., DeSeq, to measure fold-enrichment and depletion while using the statistical power that comes from biological replicates and their intrinsic dispersion. FIG. 6 shows the results of this analysis with the top 30 "genes" that are enriched after column purification. Interestingly, all of these most enriched genes mapped back to a single peptide toxin (alpha-Bungarotoxin, aBGTx). The signal to noise of this enrichment was strong, with some variants enriched >15-fold. Other toxin combinations were pulled down as well. However, compared to the input library they were not enriched, and could be fully explained by the occasional cross-packaging, e.g., a viral capsid with aBGTx displayed packaging viral genome encoding another toxin. In line with this hypothesis, all nonaBGTx members were pulled down at exactly their input proportions, which indicated random sampling at the packaging stage. Aside from the peptide toxin, the choice of secretion signal correlated strongest with whether the gene was enriched or not (see FIG. 7). No discernable patterns were immediately obvious. Linkers (connecting the toxin to VP2) on the other hand seemed to matter less, with no clear preference for length, structure, or chemical composition although linkers that contain bulky side chain were mildly selected against. The screen produced a rank ordered list of toxin-VP2 fusion proteins that are displayed on the virus surface.

To establish that the displayed toxin does not interfere with infectivity, virus (Virus A) for the most promising candidates was produced and tested for the ability to infect cultured hippocampal neurons. Non-infectious virus ($AAV_{min}$(HA/DHBD), and eAAV produced in the presence of a toxin-VP2 fusion that was not enriched in the screen described above (eAAV@PnIB) were also produced. Cultured hippocampal neurons were infected with virus at day 5 in culture, and expression was monitored for 14 days. As expected $AAV_{min}$(HA/DHBD and eAAV@PnIB did not show expression even after 14 days in vitro, whereas very strong expression was observed with eAAV@aBGTx. This indicated that the peptide toxin does not interfere with infection and subsequent steps in the viral gene delivery sequence.

Thus, there is evidence that cysteine-rich peptide toxins can be functionally expressed on the extracellular face of AAV viral capsid, which indicates that these hard-to-fold proteins were routed through the required sub-cellular compartments for assembly into functional viral capsids during recombinant virus production.

In summary, a rigorous and unbiased screen was completed for peptide toxins, linkers, and trafficking signals that are compatible with displaying peptide toxins on the surface of AAV. From this screen, eAAV candidates were identified and tested for infectivity in vitro. eAAVs were indeed infectious, suggesting that modifying the capsid surface with peptide toxins does not interfere with gene delivery.

REFERENCES

Al-Sabi et al., *J. Gen. Physiol.,* 136:273 (2010).
Arenkiel et al., *Neuron.,* 54:205 (2007)
Atasoy et al., *J. Neurosci.,* 28:7025 (2008).
Auer et al., *Nat. Methods,* 7:229 (2010).
Banta et al., *Annu. Rev. Biomed. Eng.,* 15:93 (2013).
Bayrhuber et al., *J Biol Chem.,* 280:23766 (2005).
Bennett et al., *Lancet Neurol.,* 13:587 (2014).
Bernard et al., *Science,* 305:532 (2004).
Bliss et al., *Nature,* 361:31 (1993).
Boccaccio et al., *J. Gen. Physiol.,* 124:71 (2004).
Caterina et al., *Annu. Rev. Neurosci.,* 24:487 (2001).
Christie et al., *J. Biol. Chem.,* 287:22295 (2012).
Corzo et al., *Cell Mol Life Sci.,* 60:2409 (2003).
Dayton et al., *Exp. Opin Biol Ther. Informa,* 12:757 (2012).
Delmas et al., *Nat. Rev. Neurosci.,* 12:139 (2011).
Dowell et al., *J. Neurosci.,* 23:8445 (2003).
Doya, *Nat. Neurosci.,* 11:410 (2008).
Engler et al., *PLoS ONE,* 4:e5553 (2009).
Escoubas et al., *J. Biol. Chem.,* 275:25116 (2000).
Fenno et al., *Nat. Methods*, 11:763 (2014).
Gong et al., *Nature,* 425:917 (2003).
Grieger et al., *Nat. Protoc.,* 1: 1412 (2006).
Grimm et al., *Curr. Gene Ther.* 3:281 (2003).
Grimm et al., *J. Virol.,* 82:5887 (2008).
Grosse et al., *J. Neurosci.,* 20:1869 (2000).
Gurda et al., *J. Virol.,* 86:7739 (2012).
Hagen et al., *Sci Rep.,* 4:3759 (2014).
Hioki et al., *Gene Ther.,* 14:872 (2007).
Ibanez-Tallon et al., *Neuron.,* 43:305 (2004).
Janes, *Curr. Opin. Pharmacol.,* 5:280 (2005).
Judd et al., *Mol. Ther. Nucleic Acids,* 1:e54 (2012).
Kawashima *Front Neural Circuits,* 8:37 (2014).
Klapoetke et al., *Nat. Methods,* 11:338 (2014).
Koh et al., *Cell. Mol. Life Sci.,* 63:3030 (2006).
Konermann et al., *Nature* 500:472 (2013).
Kuhlman et al., *PLoS ONE,* 3:e2005 (2008).
Kullmann, *Annu. Rev. Neurosci.,* 33:151 (2010).
Lee et al., *Biochemistry,* 49:5134 (2010).
Lee et al., *Cell,* 157:1393 (2014).
Lee et al., *Nature,* 430:232 (2004).
Lein et al., *Nature,* 445:168 (2007).
Li et al., *Proc. Natl. Acad. Sci. USA,* 90:1460 (1993).
Loiler et al., *Gene Ther.,* 10:1551 (2003).
Luan et al., *Neuron.,* 52:425 (2006).
Martin-Moutot et al., *Mol. Pharmacol.,* 69: 1931 (2006).
Matsushita et al., *J. Neurochem.,* 82:295 (2002).
Mayford et al., *Proc. Natl. Acad. Sci. USA,* 93:13250 (1996).
McGehee et al., *Annu. Rev. Physiol.,* 57:521 (1995).
McIntosh et al., *J. Biol. Chem.,* 270:16796 (1995).
Michelfelder et al., *EXD. Hematol.,* 35:1766 (2007).
Miyamoto et al., *J. Neurosci.,* 21:750 (2001).
Mohn et al., *Cell,* 98:427 (1999).
Müller et al., *Nat. Biotechnol.,* 21:1040 (2003).
Nagy *Genesis,* 26:99 (2000).
Nirthanan et al., *J. Pharmacol. Sci.,* 94:1 (2004).
Nonnenmacher et al., *Gene Ther.,* 19:649 (2012).
Osaka et al., *J. Biol. Chem.,* 274:9581 (1999).
Poulin et al., *J. Virol.,* 84:10074 (2010).
Robertson et al., *FEBS Lett.,* 383:26 (1996).

Ryan et al., *Neuron.*, 68:282 (2010).
Schmidt et al., *Nat. Commun.*, 5:3019 (2014).
Seisenberger et al., *Science*, 294:1929 (2001).
Son et al., *J. Comp. Neurol.*, 511:286 (2008).
Soto et al., *Commun. Integr. Biol.*, 7:e27887 (2014).
Stocker et al., *J. Neurosci.*, 17:3002 (1997).
Sudweeks et al., *J. Physiol.*, 527:515 (2000).
Swartz et al., *Neuron.*, 18:665 (1997a).
Swartz et al., *Neuron.*, 18:675 (1997b).
Taniguchi et al., *Neuron.*, 71:995 (2011).
Terlau et al., *Physiol Rev.*, 84:41 (2004).
Tye et al., *Nat. Rev. Neurosci.*, 13:251 (2012).
Warrington et al., *J. Virol.*, 78:6595 (2004)
Waxman, *Trends Mol. Med.*, 19:406 (2013).
Weidle et al., *Cancer Gen. Prot.*, 10(4):155 (2013).
Wells et al., *J. Neurosci. Methods*, 108:111 (2001).
Wemmie et al., *Nat. Rev. Neurosci.*, 14:461 (2013).
Wu et al., *J. Virol.*, 74:8635 (2000).
Xie et al., *Nature*, 410:936 (2001).
Xie et al., *Proc. Natl. Acad. Sci. USA*, 99:10405 (2002).
Zhao et al., *Nat. Methods*, 8:745 (2011).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to prepare a plurality of vectors comprising DNA encoding a recombinant adeno-associated virus (AAV) VP2 capsid protein that comprises a peptide toxin that binds to a molecule of a eukaryotic cell, comprising:
   a) providing a DNA encoding at least one peptide toxin that binds to a eukaryotic cell, a DNA encoding at least one sorting signal, a DNA encoding at least one peptide linker, and a DNA encoding the VP2 of an AAV; and
   b) combining in a ligation reaction the DNA encoding the at least one peptide toxin, the DNA encoding the at least one sorting signal, the DNA encoding the at least one peptide linker, the DNA encoding the VP2 of the AAV, and a hast vector, thereby yielding a plurality of ligated DNA vectors having the host vector ligated to the DNA encoding the at least one peptide sorting signal ligated to the DNA encoding the at least one peptide toxin ligated to the DNA encoding the at least one peptide linker ligated to the DNA encoding the VP2, wherein the plurality of ligated DNA vectors encode an AAV VP2 having the peptide toxin that binds to the eukaryotic cell.

2. The method of claim 1 wherein the at least one peptide toxin binds to an ion channel protein, a voltage-dependent K+ channel, or a nicotinic acetylcholine receptor.

3. The method of claim 1 wherein the AAV is AAV1, AAV2, AAV5, AAV6, AAV8, AAV9, AAV10, or AAV-DJ.

4. The method of claim 1 wherein a heparan binding domain (HBD) or a laminin binding domain in the VP2 is deleted or mutated to decrease binding to proteoglycans or laminin.

5. The method of claim 1 wherein the at least one of the linkers forms an alpha-helical structure.

6. The method of claim 1 wherein the at least one peptide toxin binds to a chloride channel protein.

7. The method of claim 1 further comprising contacting cells with the ligated DNA vectors.

8. The method of claim 7 further comprising contacting the cells with one or more vectors encoding a rAAV genome, adenovirus proteins E2A, E4 and VA, and AAV VP1 and VP3 so as to produce AAV with altered tropism.

9. The method of claim 1 wherein the DNA encoding the at least one peptide toxin encodes a peptide that is less than 200 amino acids in length.

10. A composition comprising helper-virus free recombinant AAV(rAAV) comprising a chimeric capsid protein comprising a peptide toxin that binds to a molecule of a eukaryotic cell and VP2, and a rAAV genome, wherein the peptide toxin comprises PcTx1, MITx, Mambalgin-3, Mambalgin-1, APETx2, µ-CNTX-Pn1a, µO-CNTX MrVIB, µ-CNTX SIIIA, ProTx-I, Pterinotoxin-1, VSTX3, ω-CNTX MVIIA, DTX-K, αDTX, DTX-I, Hemitoxin, Charybdotoxin, κ-CNTX RIIIJ, TsTXK-α, GxTx, HaTx, VSTx1, CONK1, κ-PVIIA, α-CNTX PIA, α-BGTx, α-CNTX GID, α-CNTX PnIB, α-CNTX IMI, SLURP-1, or α-BGTx(V31 iso), or wherein the peptide toxin binds to a N-methyl-D-aspartate (NMDA) receptor.

11. The composition of claim 10 wherein the peptide toxin binds to a voltage-dependent $Ca^{2+}$ (Cav) channel protein, an α-Amino-3-hydroxy-5-methyl-4-isoxazolepropionic acid (AMPA) receptor, an A-type voltage-dependent $K^+$ channel protein (Kv1), a voltage-dependent $Na^+$ channel Nav1.8 protein, a vanilloid receptor1 (TRPV1), or an acid-sensing ion channel (ASIC) protein.

12. The composition of claim 10 wherein the peptide toxin binds to an ASCII protein, an ASIC3 protein, a Nav 1.8 protein, a Kv1.2 protein, or an α7 nicotinic acetylcholine receptor (nAChR).

13. The composition of claim 10 wherein the peptide toxin binds to a pH or a voltage sensitive channel protein.

14. The composition of claim 10 wherein the rAAV genome encodes a therapeutic or a prophylactic gene product.

15. The composition of claim 10 wherein the VP2 is from AAV1, AAV2, AAV5, AAV6, AAV8, AAV9, AAV-DJ, or AAV10.

16. The composition of claim 10 wherein the rAAV genome is from AAV1, AAV2, AAV5, AAV6, AAV8, AAV9, or AAV10.

17. A method to prepare helper free recombinant AAV the capsid of which comprises a peptide toxin that binds to a molecule of a eukaryotic cell, comprising: providing one or more vectors having a rAAV genome, nucleic acid encoding AAV VP1, AAY VP3, adenovirus E2A, adenovirus E4 and adenovirus VA and a host vector having an open reading frame comprising a DNA encoding at least one peptide sorting signal operably linked to a DNA encoding at least one peptide toxin which binds to the molecule of a eukaryotic cell operably linked to a DNA encoding the at least one peptide linker operably inked to a DNA encoding AAV VP2; and contacting a cell with the one or more vectors and the host vector in an amount that generates the helper free rAAV with a capsid having the peptide toxin.

18. The method of claim 17 wherein the at least one peptide toxin is PcTx1, Mambalgin, APETx2, µO-CNTX MrVIB, µ-CNTX SIIIA, ProTx-I, Pterinotoxin, VSTXe, αDTX, DTX-I, Hemitoxin, κ-CNTX RIIIJ, TsTX-K-α, or α-BGTx (V31 isoform).

19. The method of claim 17 wherein the at least one peptide sorting signal comprises at least one of MGWSCI-ILFLVATATGAHS (SEQ ID NO:1), MSTMRLLTLALLF-SCSVA (SEQ ID NO:2), MSTMHLLTFALLFSCSFARA (SEQ ID NO:3), MQHIFAFFCTGFLGAVVG (SEQ ID NO:4), MKPSAECCSPKFWLVLAVLAVSGSKA (SEQ ID NO:5), MSALLILALVGAAVA (SEQ ID NO:6), MDVCVRLALWLLWGLLLHQGQS (SEQ ID NO:7), MKLCILLAVVAFVGLSLG(SEQ ID NO:8), MKLSLVAAMLLLLSAARA (SEQ ID NO:9), MLLSVPLLLGLLGLAVA (SEQ ID NO:10), MQKIMHISVLLSPVLWGLIFGVSS (SEQ ID NO: 11), MKTIIALSYIFCLVFA (SEQ ID NO:12), MRCSPGGVWLALAASLLHVSLQ (SEQ ID NO:13), MATGSRTSLLLAFGLLCLPWLQEGSA (SEQ ID NO:14), MDSKGSSQKGSRLLLLLVVSNLLLCQGVVS (SEQ ID NO:15), MWPLVAALLLGSACCGSA(SEQ ID NO:16), MVCFRLFPVPGSGLVLVCLVLGAVRSYA(SEQ ID NO:17), MRLAVGALLVCAVLGLCLA (SEQ ID NO:18), MRGTPLLLVVSLFSLLQD (SEQ ID NO:19), MGLRALMLWLLAAAGLVRESLQG (SEQ ID NO:20), MDYGGALSAVGRELL(SEQ ID NO:21), MPPL-LAPLLCLALLPALA (SEQ ID NO:22), MGAMAPRTLLLLLAAALAPTQRA(SEQ ID NO:23) or a fragment thereof that provides substantially the same activity as one of SEQ ID Nos. 1 to 23.

20. The method of claim 17 wherein the at least one linker comprises GSAG (SEQ ID NO:24), GSAGSAG (SEQ ID NO:25), GSAGSAGSAG (SEQ ID NO:26), GSAGSAGSAGGSAGSAG (SEQ ID NO:27), AAADYKDDDDKIDAAAGGALCN (SEQ ID NO:28), IDYKDDDDKLAAAGNGNGNGNGNGNGDGNG-GALCN (SEQ ID NO:29), PPPPPPPPPPPPPPP (SEQ ID NO:30), GNGN (SEQ ID NO:31), GNGNAGNGN (SEQ ID NO:32), GNGNAGNGNAGNGNAGNGN (SEQ ID NO:33), AEAAAKA (SEQ ID NO:34), AEAAAKEAAAKA (SEQ ID NO:35), AEAAAKEAAAKEAAAKA (SEQ ID NO:36), AEAAAKEAAAKEAAAKEAAAKA (SEQ ID NO:37), PDANLRPEDLW(SEQ ID NO:38), PDANLRPEDL-WANHSKVV (SEQ ID NO:39), PDANLRPEDLWANHS-KVVPLPKPPHMKDSA (SEQ ID NO:40), EEEEKKKQQEEEAERLRRIQEEMEKERKRREEDE-KRRRKEEEERRMKLEMEAKRKQEEEE RKKRED-DEKRKKK(SEQ ID NO:41),
 EEEEKKKEEEEKKQKEEQERLAKEEAERKQKE-
  EQERLERERKEREEQEKKAKEEAE RIAKLE-
  AEKKAEEERKAKEEEERKAKEEEERKKKE-
  EQERLAKEKEEAERKAAEEKKAKEE
  QERKEKEEAERKQR(SEQ ID NO:42), or
 EEEEKKKEEEEKKQKEEQERLAKEEAERKQKE-
  EQERLAKEEAERKQKEEEERKQKE EEERKQ-
  KEEEERKLKEEQERKAAEEKKAKEEAERKAKE-
  EQERKAEEERKKKEEEERLERE RKEREEQE- KKAKEEAERIAKLEAEKKAEEERKAKEEEER-
KAKEEEERKKKEEQERLAKEK EEAERKAAEEK-
KAKEEQER KEKEEAERKQR (SEQ ID NO:43).

\* \* \* \* \*

SEQUENCE LISTING

```
<160> NUMBER OF SEQ ID NOS: 66

<210> SEQ ID NO 1
<211> LENGTH: 19
<212> TYPE: PRT
<213> ORGANISM: Artificial Sequence
<220> FEATURE:
<223> OTHER INFORMATION: A synthetic peptide sorting signal

<400> SEQUENCE: 1

Met Gly Trp Ser Cys Ile Ile Leu Phe Leu Val Ala Thr Ala Thr Gly
1               5                   10                  15

Ala His Ser

<210> SEQ ID NO 2
<211> LENGTH: 18
<212> TYPE: PRT
<213> ORGANISM: Artificial Sequence
<220> FEATURE:
<223> OTHER INFORMATION: A synthetic peptide sorting signal

<400> SEQUENCE: 2

Met Ser Thr Met Arg Leu Leu Thr Leu Ala Leu Leu Phe Ser Cys Ser
1               5                   10                  15

Val Ala

<210> SEQ ID NO 3
<211> LENGTH: 20
<212> TYPE: PRT
<213> ORGANISM: Artificial Sequence
<220> FEATURE:
<223> OTHER INFORMATION: A synthetic peptide sorting signal

<400> SEQUENCE: 3

Met Ser Thr Met His Leu Leu Thr Phe Ala Leu Leu Phe Ser Cys Ser
1               5                   10                  15

Phe Ala Arg Ala
            20

<210> SEQ ID NO 4
<211> LENGTH: 18
<212> TYPE: PRT
<213> ORGANISM: Artificial Sequence
<220> FEATURE:
<223> OTHER INFORMATION: A synthetic peptide sorting signal

<400> SEQUENCE: 4

Met Gln His Ile Phe Ala Phe Phe Cys Thr Gly Phe Leu Gly Ala Val
```

-continued

```
1               5                   10                  15

Val Gly

<210> SEQ ID NO 5
<211> LENGTH: 26
<212> TYPE: PRT
<213> ORGANISM: Artificial Sequence
<220> FEATURE:
<223> OTHER INFORMATION: A synthetic peptide sorting signal

<400> SEQUENCE: 5

Met Lys Pro Ser Ala Glu Cys Cys Ser Pro Lys Phe Trp Leu Val Leu
1               5                   10                  15

Ala Val Leu Ala Val Ser Gly Ser Lys Ala
            20                  25

<210> SEQ ID NO 6
<211> LENGTH: 15
<212> TYPE: PRT
<213> ORGANISM: Artificial Sequence
<220> FEATURE:
<223> OTHER INFORMATION: A synthetic peptide sorting signal

<400> SEQUENCE: 6

Met Ser Ala Leu Leu Ile Leu Ala Leu Val Gly Ala Ala Val Ala
1               5                   10                  15

<210> SEQ ID NO 7
<211> LENGTH: 22
<212> TYPE: PRT
<213> ORGANISM: Artificial Sequence
<220> FEATURE:
<223> OTHER INFORMATION: A synthetic peptide sorting signal

<400> SEQUENCE: 7

Met Asp Val Cys Val Arg Leu Ala Leu Trp Leu Leu Trp Gly Leu Leu
1               5                   10                  15

Leu His Gln Gly Gln Ser
            20

<210> SEQ ID NO 8
<211> LENGTH: 18
<212> TYPE: PRT
<213> ORGANISM: Artificial Sequence
<220> FEATURE:
<223> OTHER INFORMATION: A synthetic peptide sorting signal

<400> SEQUENCE: 8

Met Lys Leu Cys Ile Leu Leu Ala Val Val Ala Phe Val Gly Leu Ser
1               5                   10                  15

Leu Gly

<210> SEQ ID NO 9
<211> LENGTH: 18
<212> TYPE: PRT
<213> ORGANISM: Artificial Sequence
<220> FEATURE:
<223> OTHER INFORMATION: A synthetic peptide sorting signal

<400> SEQUENCE: 9

Met Lys Leu Ser Leu Val Ala Ala Met Leu Leu Leu Leu Ser Ala Ala
1               5                   10                  15

Arg Ala
```

```
<210> SEQ ID NO 10
<211> LENGTH: 17
<212> TYPE: PRT
<213> ORGANISM: Artificial Sequence
<220> FEATURE:
<223> OTHER INFORMATION: A synthetic peptide sorting signal

<400> SEQUENCE: 10

Met Leu Leu Ser Val Pro Leu Leu Gly Leu Leu Gly Leu Ala Val
1               5                   10                  15

Ala

<210> SEQ ID NO 11
<211> LENGTH: 24
<212> TYPE: PRT
<213> ORGANISM: Artificial Sequence
<220> FEATURE:
<223> OTHER INFORMATION: A synthetic peptide sorting signal

<400> SEQUENCE: 11

Met Gln Lys Ile Met His Ile Ser Val Leu Leu Ser Pro Val Leu Trp
1               5                   10                  15

Gly Leu Ile Phe Gly Val Ser Ser
            20

<210> SEQ ID NO 12
<211> LENGTH: 16
<212> TYPE: PRT
<213> ORGANISM: Artificial Sequence
<220> FEATURE:
<223> OTHER INFORMATION: A synthetic peptide sorting signal

<400> SEQUENCE: 12

Met Lys Thr Ile Ile Ala Leu Ser Tyr Ile Phe Cys Leu Val Phe Ala
1               5                   10                  15

<210> SEQ ID NO 13
<211> LENGTH: 22
<212> TYPE: PRT
<213> ORGANISM: Artificial Sequence
<220> FEATURE:
<223> OTHER INFORMATION: A synthetic peptide sorting signal

<400> SEQUENCE: 13

Met Arg Cys Ser Pro Gly Gly Val Trp Leu Ala Leu Ala Ala Ser Leu
1               5                   10                  15

Leu His Val Ser Leu Gln
            20

<210> SEQ ID NO 14
<211> LENGTH: 26
<212> TYPE: PRT
<213> ORGANISM: Artificial Sequence
<220> FEATURE:
<223> OTHER INFORMATION: A synthetic peptide sorting signal

<400> SEQUENCE: 14

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 15
<211> LENGTH: 30
```

```
<212> TYPE: PRT
<213> ORGANISM: Artificial Sequence
<220> FEATURE:
<223> OTHER INFORMATION: A synthetic peptide sorting signal

<400> SEQUENCE: 15

Met Asp Ser Lys Gly Ser Ser Gln Lys Gly Ser Arg Leu Leu Leu
1               5                   10                  15

Leu Val Val Ser Asn Leu Leu Leu Cys Gln Gly Val Val Ser
            20                  25                  30

<210> SEQ ID NO 16
<211> LENGTH: 18
<212> TYPE: PRT
<213> ORGANISM: Artificial Sequence
<220> FEATURE:
<223> OTHER INFORMATION: A synthetic peptide sorting signal

<400> SEQUENCE: 16

Met Trp Pro Leu Val Ala Ala Leu Leu Leu Gly Ser Ala Cys Cys Gly
1               5                   10                  15

Ser Ala

<210> SEQ ID NO 17
<211> LENGTH: 28
<212> TYPE: PRT
<213> ORGANISM: Artificial Sequence
<220> FEATURE:
<223> OTHER INFORMATION: A synthetic peptide sorting signal

<400> SEQUENCE: 17

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala
            20                  25

<210> SEQ ID NO 18
<211> LENGTH: 19
<212> TYPE: PRT
<213> ORGANISM: Artificial Sequence
<220> FEATURE:
<223> OTHER INFORMATION: A synthetic peptide sorting signal

<400> SEQUENCE: 18

Met Arg Leu Ala Val Gly Ala Leu Leu Val Cys Ala Val Leu Gly Leu
1               5                   10                  15

Cys Leu Ala

<210> SEQ ID NO 19
<211> LENGTH: 18
<212> TYPE: PRT
<213> ORGANISM: Artificial Sequence
<220> FEATURE:
<223> OTHER INFORMATION: A synthetic peptide sorting signal

<400> SEQUENCE: 19

Met Arg Gly Thr Pro Leu Leu Leu Val Val Ser Leu Phe Ser Leu Leu
1               5                   10                  15

Gln Asp

<210> SEQ ID NO 20
<211> LENGTH: 23
<212> TYPE: PRT
<213> ORGANISM: Artificial Sequence
```

```
<220> FEATURE:
<223> OTHER INFORMATION: A synthetic peptide sorting signal

<400> SEQUENCE: 20

Met Gly Leu Arg Ala Leu Met Leu Trp Leu Leu Ala Ala Ala Gly Leu
1               5                   10                  15

Val Arg Glu Ser Leu Gln Gly
            20

<210> SEQ ID NO 21
<211> LENGTH: 15
<212> TYPE: PRT
<213> ORGANISM: Artificial Sequence
<220> FEATURE:
<223> OTHER INFORMATION: A synthetic peptide sorting signal

<400> SEQUENCE: 21

Met Asp Tyr Gly Gly Ala Leu Ser Ala Val Gly Arg Glu Leu Leu
1               5                   10                  15

<210> SEQ ID NO 22
<211> LENGTH: 18
<212> TYPE: PRT
<213> ORGANISM: Artificial Sequence
<220> FEATURE:
<223> OTHER INFORMATION: A synthetic peptide sorting signal

<400> SEQUENCE: 22

Met Pro Pro Leu Leu Ala Pro Leu Leu Cys Leu Ala Leu Leu Pro Ala
1               5                   10                  15

Leu Ala

<210> SEQ ID NO 23
<211> LENGTH: 23
<212> TYPE: PRT
<213> ORGANISM: Artificial Sequence
<220> FEATURE:
<223> OTHER INFORMATION: A synthetic peptide sorting signal

<400> SEQUENCE: 23

Met Gly Ala Met Ala Pro Arg Thr Leu Leu Leu Leu Leu Ala Ala Ala
1               5                   10                  15

Leu Ala Pro Thr Gln Arg Ala
            20

<210> SEQ ID NO 24
<211> LENGTH: 4
<212> TYPE: PRT
<213> ORGANISM: Artificial Sequence
<220> FEATURE:
<223> OTHER INFORMATION: A synthetic peptide linker

<400> SEQUENCE: 24

Gly Ser Ala Gly
1

<210> SEQ ID NO 25
<211> LENGTH: 7
<212> TYPE: PRT
<213> ORGANISM: Artificial Sequence
<220> FEATURE:
<223> OTHER INFORMATION: A synthetic peptide linker

<400> SEQUENCE: 25

Gly Ser Ala Gly Ser Ala Gly
```

```
<210> SEQ ID NO 26
<211> LENGTH: 10
<212> TYPE: PRT
<213> ORGANISM: Artificial Sequence
<220> FEATURE:
<223> OTHER INFORMATION: A synthetic peptide linker

<400> SEQUENCE: 26

Gly Ser Ala Gly Ser Ala Gly Ser Ala Gly
1               5                   10

<210> SEQ ID NO 27
<211> LENGTH: 20
<212> TYPE: PRT
<213> ORGANISM: Artificial Sequence
<220> FEATURE:
<223> OTHER INFORMATION: A synthetic peptide linker

<400> SEQUENCE: 27

Gly Ser Ala Gly Ser Ala Gly Ser Ala Gly Gly Ser Ala Gly Ser Ala
1               5                   10                  15

Gly Ser Ala Gly
            20

<210> SEQ ID NO 28
<211> LENGTH: 22
<212> TYPE: PRT
<213> ORGANISM: Artificial Sequence
<220> FEATURE:
<223> OTHER INFORMATION: A synthetic peptide linker

<400> SEQUENCE: 28

Ala Ala Ala Asp Tyr Lys Asp Asp Asp Asp Lys Ile Asp Ala Ala Ala
1               5                   10                  15

Gly Gly Ala Leu Cys Asn
            20

<210> SEQ ID NO 29
<211> LENGTH: 37
<212> TYPE: PRT
<213> ORGANISM: Artificial Sequence
<220> FEATURE:
<223> OTHER INFORMATION: A synthetic peptide linker

<400> SEQUENCE: 29

Ile Asp Tyr Lys Asp Asp Asp Asp Lys Leu Ala Ala Ala Gly Asn Gly
1               5                   10                  15

Asn Gly Asn Gly Asn Gly Asn Gly Asn Gly Asn Gly Asp Gly Asn Gly
            20                  25                  30

Gly Ala Leu Cys Asn
        35

<210> SEQ ID NO 30
<211> LENGTH: 15
<212> TYPE: PRT
<213> ORGANISM: Artificial Sequence
<220> FEATURE:
<223> OTHER INFORMATION: A synthetic peptide linker

<400> SEQUENCE: 30

Pro Pro Pro Pro Pro Pro Pro Pro Pro Pro Pro Pro Pro
1               5                   10                  15
```

```
<210> SEQ ID NO 31
<211> LENGTH: 4
<212> TYPE: PRT
<213> ORGANISM: Artificial Sequence
<220> FEATURE:
<223> OTHER INFORMATION: A synthetic peptide linker

<400> SEQUENCE: 31

Gly Asn Gly Asn
1

<210> SEQ ID NO 32
<211> LENGTH: 9
<212> TYPE: PRT
<213> ORGANISM: Artificial Sequence
<220> FEATURE:
<223> OTHER INFORMATION: A synthetic peptide linker

<400> SEQUENCE: 32

Gly Asn Gly Asn Ala Gly Asn Gly Asn
1               5

<210> SEQ ID NO 33
<211> LENGTH: 19
<212> TYPE: PRT
<213> ORGANISM: Artificial Sequence
<220> FEATURE:
<223> OTHER INFORMATION: A synthetic peptide linker

<400> SEQUENCE: 33

Gly Asn Gly Asn Ala Gly Asn Gly Asn Ala Gly Asn Gly Asn Ala Gly
1               5                   10                  15

Asn Gly Asn

<210> SEQ ID NO 34
<211> LENGTH: 7
<212> TYPE: PRT
<213> ORGANISM: Artificial Sequence
<220> FEATURE:
<223> OTHER INFORMATION: A synthetic peptide linker

<400> SEQUENCE: 34

Ala Glu Ala Ala Ala Lys Ala
1               5

<210> SEQ ID NO 35
<211> LENGTH: 12
<212> TYPE: PRT
<213> ORGANISM: Artificial Sequence
<220> FEATURE:
<223> OTHER INFORMATION: A synthetic peptide linker

<400> SEQUENCE: 35

Ala Glu Ala Ala Ala Lys Glu Ala Ala Ala Lys Ala
1               5                   10

<210> SEQ ID NO 36
<211> LENGTH: 17
<212> TYPE: PRT
<213> ORGANISM: Artificial Sequence
<220> FEATURE:
<223> OTHER INFORMATION: A synthetic peptide linker

<400> SEQUENCE: 36

Ala Glu Ala Ala Ala Lys Glu Ala Ala Ala Lys Glu Ala Ala Ala Lys
1               5                   10                  15
```

Ala

<210> SEQ ID NO 37
<211> LENGTH: 22
<212> TYPE: PRT
<213> ORGANISM: Artificial Sequence
<220> FEATURE:
<223> OTHER INFORMATION: A synthetic peptide linker

<400> SEQUENCE: 37

```
Ala Glu Ala Ala Ala Lys Glu Ala Ala Ala Lys Glu Ala Ala Ala Lys
1               5                  10                  15

Glu Ala Ala Ala Lys Ala
            20
```

<210> SEQ ID NO 38
<211> LENGTH: 11
<212> TYPE: PRT
<213> ORGANISM: Artificial Sequence
<220> FEATURE:
<223> OTHER INFORMATION: A synthetic peptide linker

<400> SEQUENCE: 38

```
Pro Asp Ala Asn Leu Arg Pro Glu Asp Leu Trp
1               5                  10
```

<210> SEQ ID NO 39
<211> LENGTH: 18
<212> TYPE: PRT
<213> ORGANISM: Artificial Sequence
<220> FEATURE:
<223> OTHER INFORMATION: A synthetic peptide linker

<400> SEQUENCE: 39

```
Pro Asp Ala Asn Leu Arg Pro Glu Asp Leu Trp Ala Asn His Ser Lys
1               5                  10                  15

Val Val
```

<210> SEQ ID NO 40
<211> LENGTH: 30
<212> TYPE: PRT
<213> ORGANISM: Artificial Sequence
<220> FEATURE:
<223> OTHER INFORMATION: A synthetic peptide linker

<400> SEQUENCE: 40

```
Pro Asp Ala Asn Leu Arg Pro Glu Asp Leu Trp Ala Asn His Ser Lys
1               5                  10                  15

Val Val Pro Leu Pro Lys Pro Pro His Met Lys Asp Ser Ala
            20                  25                  30
```

<210> SEQ ID NO 41
<211> LENGTH: 73
<212> TYPE: PRT
<213> ORGANISM: Artificial Sequence
<220> FEATURE:
<223> OTHER INFORMATION: A synthetic peptide linker

<400> SEQUENCE: 41

```
Glu Glu Glu Glu Lys Lys Lys Gln Gln Glu Glu Ala Glu Arg Leu
1               5                  10                  15

Arg Arg Ile Gln Glu Glu Met Glu Lys Glu Arg Lys Arg Glu Glu
            20                  25                  30
```

-continued

Asp Glu Lys Arg Arg Lys Glu Glu Glu Arg Met Lys Leu
          35                  40                  45

Glu Met Glu Ala Lys Arg Lys Gln Glu Glu Arg Lys Lys Arg
 50                  55                  60

Glu Asp Asp Glu Lys Arg Lys Lys Lys
 65                  70

<210> SEQ ID NO 42
<211> LENGTH: 130
<212> TYPE: PRT
<213> ORGANISM: Artificial Sequence
<220> FEATURE:
<223> OTHER INFORMATION: A synthetic peptide linker

<400> SEQUENCE: 42

Glu Glu Glu Glu Lys Lys Lys Glu Glu Glu Lys Lys Gln Lys Glu
 1               5                  10                  15

Glu Gln Glu Arg Leu Ala Lys Glu Glu Ala Glu Arg Lys Gln Lys Glu
             20                  25                  30

Glu Gln Glu Arg Leu Glu Arg Glu Arg Lys Glu Arg Glu Glu Gln Glu
         35                  40                  45

Lys Lys Ala Lys Glu Glu Ala Glu Arg Ile Ala Lys Leu Glu Ala Glu
 50                  55                  60

Lys Lys Ala Glu Glu Glu Arg Lys Ala Lys Glu Glu Glu Glu Arg Lys
 65                  70                  75                  80

Ala Lys Glu Glu Glu Glu Arg Lys Lys Lys Glu Glu Gln Glu Arg Leu
                 85                  90                  95

Ala Lys Glu Lys Glu Glu Ala Glu Arg Lys Ala Ala Glu Glu Lys Lys
                 100                 105                 110

Ala Lys Glu Glu Gln Glu Arg Lys Glu Lys Glu Glu Ala Glu Arg Lys
             115                 120                 125

Gln Arg
     130

<210> SEQ ID NO 43
<211> LENGTH: 206
<212> TYPE: PRT
<213> ORGANISM: Artificial Sequence
<220> FEATURE:
<223> OTHER INFORMATION: A synthetic peptide linker

<400> SEQUENCE: 43

Glu Glu Glu Glu Lys Lys Lys Glu Glu Glu Lys Lys Gln Lys Glu
 1               5                  10                  15

Glu Gln Glu Arg Leu Ala Lys Glu Glu Ala Glu Arg Lys Gln Lys Glu
             20                  25                  30

Glu Gln Glu Arg Leu Ala Lys Glu Glu Ala Glu Arg Lys Gln Lys Glu
         35                  40                  45

Glu Glu Glu Arg Lys Gln Lys Glu Glu Glu Arg Lys Gln Lys Glu
 50                  55                  60

Glu Glu Glu Arg Lys Leu Lys Glu Glu Gln Glu Arg Lys Ala Ala Glu
 65                  70                  75                  80

Glu Lys Lys Ala Lys Glu Glu Ala Glu Arg Lys Ala Lys Glu Glu Gln
                 85                  90                  95

Glu Arg Lys Ala Glu Glu Glu Arg Lys Lys Lys Glu Glu Glu Glu Arg
             100                 105                 110

Leu Glu Arg Glu Arg Lys Glu Arg Glu Glu Gln Glu Lys Lys Ala Lys
         115                 120                 125

Glu Glu Ala Glu Arg Ile Ala Lys Leu Glu Ala Glu Lys Lys Ala Glu
            130                 135                 140

Glu Glu Arg Lys Ala Lys Glu Glu Glu Arg Lys Ala Lys Glu Glu
145                 150                 155                 160

Glu Glu Arg Lys Lys Lys Glu Glu Gln Glu Arg Leu Ala Lys Glu Lys
                165                 170                 175

Glu Glu Ala Glu Arg Lys Ala Ala Glu Glu Lys Lys Ala Lys Glu Glu
            180                 185                 190

Gln Glu Arg Lys Glu Lys Glu Glu Ala Glu Arg Lys Gln Arg
        195                 200                 205

<210> SEQ ID NO 44
<211> LENGTH: 65
<212> TYPE: PRT
<213> ORGANISM: Artificial Sequence
<220> FEATURE:
<223> OTHER INFORMATION: A synthetic peptide toxin

<400> SEQUENCE: 44

Leu Thr Cys Val Lys Ser Asn Ser Ile Trp Phe Pro Thr Ser Glu Asp
1               5                   10                  15

Cys Pro Asp Gly Gln Asn Leu Cys Phe Lys Arg Trp Gln Tyr Ile Ser
            20                  25                  30

Pro Arg Met Tyr Asp Phe Thr Arg Gly Cys Ala Ala Thr Cys Pro Lys
        35                  40                  45

Ala Glu Tyr Arg Asp Val Ile Asn Cys Cys Gly Thr Asp Lys Cys Asn
    50                  55                  60

Lys
65

<210> SEQ ID NO 45
<211> LENGTH: 36
<212> TYPE: PRT
<213> ORGANISM: Artificial Sequence
<220> FEATURE:
<223> OTHER INFORMATION: A synthetic peptide toxin

<400> SEQUENCE: 45

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 46
<211> LENGTH: 65
<212> TYPE: PRT
<213> ORGANISM: Artificial Sequence
<220> FEATURE:
<223> OTHER INFORMATION: A synthetic peptide toxin

<400> SEQUENCE: 46

Leu Thr Cys Val Lys Ser Asn Ser Ile Trp Phe Pro Thr Ser Glu Asp
1               5                   10                  15

Cys Pro Asp Gly Gln Asn Leu Cys Phe Lys Arg Trp Gln Tyr Ile Ser
            20                  25                  30

Pro Arg Met Tyr Asp Phe Thr Arg Gly Cys Ala Ala Thr Cys Pro Lys
        35                  40                  45

```
Ala Glu Tyr Arg Asp Val Ile Asn Cys Cys Gly Thr Asp Lys Cys Asn
        50                  55                  60

Lys
65

<210> SEQ ID NO 47
<211> LENGTH: 36
<212> TYPE: PRT
<213> ORGANISM: Artificial Sequence
<220> FEATURE:
<223> OTHER INFORMATION: A synthetic peptide toxin

<400> SEQUENCE: 47

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 48
<211> LENGTH: 40
<212> TYPE: PRT
<213> ORGANISM: Artificial Sequence
<220> FEATURE:
<223> OTHER INFORMATION: A synthetic peptide toxin

<400> SEQUENCE: 48

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Arg Ser Phe Glu Val
            20                  25                  30

Cys Val Pro Lys Thr Pro Lys Thr
            35                  40

<210> SEQ ID NO 49
<211> LENGTH: 57
<212> TYPE: PRT
<213> ORGANISM: Artificial Sequence
<220> FEATURE:
<223> OTHER INFORMATION: A synthetic peptide toxin

<400> SEQUENCE: 49

Leu Lys Cys Tyr Gln His Gly Lys Val Val Thr Cys His Arg Asp Met
1               5                   10                  15

Lys Phe Cys Tyr His Asn Thr Gly Met Pro Phe Arg Asn Leu Lys Leu
            20                  25                  30

Ile Leu Gln Gly Cys Ser Ser Cys Ser Glu Thr Glu Asn Asn Lys
            35                  40                  45

Cys Cys Ser Thr Asp Arg Cys Asn Lys
        50                  55

<210> SEQ ID NO 50
<211> LENGTH: 42
<212> TYPE: PRT
<213> ORGANISM: Artificial Sequence
<220> FEATURE:
<223> OTHER INFORMATION: A synthetic peptide toxin

<400> SEQUENCE: 50

Gly Thr Ala Cys Ser Cys Gly Asn Ser Lys Gly Ile Tyr Trp Phe Tyr
1               5                   10                  15
```

```
Arg Pro Ser Cys Pro Thr Asp Arg Gly Tyr Thr Gly Ser Cys Arg Tyr
            20                  25                  30

Phe Leu Gly Thr Cys Cys Thr Pro Ala Asp
        35                  40
```

<210> SEQ ID NO 51
<211> LENGTH: 20
<212> TYPE: PRT
<213> ORGANISM: Artificial Sequence
<220> FEATURE:
<223> OTHER INFORMATION: A synthetic peptide toxin

<400> SEQUENCE: 51

```
Gln Asn Cys Cys Asn Gly Gly Cys Ser Ser Lys Trp Cys Arg Asp His
1               5                   10                  15

Ala Arg Cys Cys
            20
```

<210> SEQ ID NO 52
<211> LENGTH: 35
<212> TYPE: PRT
<213> ORGANISM: Artificial Sequence
<220> FEATURE:
<223> OTHER INFORMATION: A synthetic peptide toxin

<400> SEQUENCE: 52

```
Glu Cys Arg Tyr Trp Leu Gly Gly Cys Ser Ala Gly Gln Thr Cys Cys
1               5                   10                  15

Lys His Leu Val Cys Ser Arg Arg His Gly Trp Cys Val Trp Asp Gly
            20                  25                  30

Thr Phe Ser
        35
```

<210> SEQ ID NO 53
<211> LENGTH: 34
<212> TYPE: PRT
<213> ORGANISM: Artificial Sequence
<220> FEATURE:
<223> OTHER INFORMATION: A synthetic peptide toxin

<400> SEQUENCE: 53

```
Asp Asp Cys Leu Gly Met Phe Ser Ser Cys Asp Pro Asp Asn Asp Lys
1               5                   10                  15

Cys Cys Glu Gly Arg Lys Cys Asn Arg Lys Asp Lys Trp Cys Lys Tyr
            20                  25                  30

Val Leu
```

<210> SEQ ID NO 54
<211> LENGTH: 34
<212> TYPE: PRT
<213> ORGANISM: Artificial Sequence
<220> FEATURE:
<223> OTHER INFORMATION: A synthetic peptide toxin

<400> SEQUENCE: 54

```
Asp Cys Leu Gly Trp Phe Lys Gly Cys Asp Pro Asp Asn Asp Lys Cys
1               5                   10                  15

Cys Glu Gly Tyr Lys Cys Asn Arg Arg Asp Lys Trp Cys Lys Tyr Lys
            20                  25                  30

Leu Trp
```

<210> SEQ ID NO 55

<211> LENGTH: 59
<212> TYPE: PRT
<213> ORGANISM: Artificial Sequence
<220> FEATURE:
<223> OTHER INFORMATION: A synthetic peptide toxin

<400> SEQUENCE: 55

```
Gln Pro Arg Arg Lys Leu Cys Ile Leu His Arg Asn Pro Gly Arg Cys
1               5                   10                  15

Tyr Asp Lys Ile Pro Ala Phe Tyr Tyr Asn Gln Lys Lys Lys Gln Cys
            20                  25                  30

Glu Arg Phe Asp Trp Ser Gly Cys Gly Gly Asn Ser Asn Arg Phe Lys
        35                  40                  45

Thr Ile Glu Glu Cys Arg Arg Thr Cys Ile Gly
    50                  55
```

<210> SEQ ID NO 56
<211> LENGTH: 60
<212> TYPE: PRT
<213> ORGANISM: Artificial Sequence
<220> FEATURE:
<223> OTHER INFORMATION: A synthetic peptide toxin

<400> SEQUENCE: 56

```
Gln Pro Leu Arg Lys Leu Cys Ile Leu His Arg Asn Pro Gly Arg Cys
1               5                   10                  15

Tyr Gln Lys Ile Pro Ala Phe Tyr Tyr Asn Gln Lys Lys Lys Gln Cys
            20                  25                  30

Glu Gly Phe Thr Trp Ser Gly Cys Gly Gly Asn Ser Asn Arg Phe Lys
        35                  40                  45

Thr Ile Glu Glu Cys Arg Arg Thr Cys Ile Arg Lys
    50                  55                  60
```

<210> SEQ ID NO 57
<211> LENGTH: 35
<212> TYPE: PRT
<213> ORGANISM: Artificial Sequence
<220> FEATURE:
<223> OTHER INFORMATION: A synthetic peptide toxin

<400> SEQUENCE: 57

```
Ile Lys Cys Thr Leu Ser Lys Asp Cys Tyr Ser Pro Cys Lys Lys Glu
1               5                   10                  15

Thr Gly Cys Pro Arg Ala Lys Cys Ile Asn Arg Asn Cys Lys Cys Tyr
            20                  25                  30

Gly Cys Ser
        35
```

<210> SEQ ID NO 58
<211> LENGTH: 25
<212> TYPE: PRT
<213> ORGANISM: Artificial Sequence
<220> FEATURE:
<223> OTHER INFORMATION: A synthetic peptide toxin

<400> SEQUENCE: 58

```
Leu Pro Pro Cys Cys Thr Pro Pro Lys Lys His Cys Pro Ala Pro Ala
1               5                   10                  15

Cys Lys Tyr Lys Pro Cys Cys Lys Ser
            20                  25
```

<210> SEQ ID NO 59

```
<211> LENGTH: 37
<212> TYPE: PRT
<213> ORGANISM: Artificial Sequence
<220> FEATURE:
<223> OTHER INFORMATION: A synthetic peptide toxin

<400> SEQUENCE: 59

Val Phe Ile Asn Ala Lys Cys Arg Gly Ser Pro Glu Cys Leu Pro Lys
1               5                   10                  15

Cys Lys Glu Ala Ile Gly Lys Ala Ala Gly Lys Cys Met Asn Gly Lys
            20                  25                  30

Cys Lys Cys Tyr Pro
        35

<210> SEQ ID NO 60
<211> LENGTH: 74
<212> TYPE: PRT
<213> ORGANISM: Artificial Sequence
<220> FEATURE:
<223> OTHER INFORMATION: A synthetic peptide toxin

<400> SEQUENCE: 60

Ile Val Cys His Thr Thr Ala Thr Ser Pro Ile Ser Ala Val Thr Cys
1               5                   10                  15

Pro Pro Gly Glu Asn Leu Cys Tyr Arg Lys Met Trp Cys Asp Val Phe
            20                  25                  30

Cys Ser Ser Arg Gly Lys Val Val Glu Leu Gly Cys Ala Ala Thr Cys
        35                  40                  45

Pro Ser Lys Lys Pro Tyr Glu Glu Val Thr Cys Cys Ser Thr Asp Lys
    50                  55                  60

Cys Asn Pro His Pro Lys Gln Arg Pro Gly
65                  70

<210> SEQ ID NO 61
<211> LENGTH: 19
<212> TYPE: PRT
<213> ORGANISM: Artificial Sequence
<220> FEATURE:
<223> OTHER INFORMATION: A synthetic peptide toxin

<400> SEQUENCE: 61

Ile Arg Asp Glu Cys Cys Ser Asn Pro Ala Cys Arg Val Asn Asn Pro
1               5                   10                  15

His Val Cys

<210> SEQ ID NO 62
<211> LENGTH: 16
<212> TYPE: PRT
<213> ORGANISM: Artificial Sequence
<220> FEATURE:
<223> OTHER INFORMATION: A synthetic peptide toxin

<400> SEQUENCE: 62

Gly Cys Cys Ser Leu Pro Pro Cys Ala Leu Ser Asn Pro Asp Tyr Cys
1               5                   10                  15

<210> SEQ ID NO 63
<211> LENGTH: 12
<212> TYPE: PRT
<213> ORGANISM: Artificial Sequence
<220> FEATURE:
<223> OTHER INFORMATION: A synthetic peptide toxin

<400> SEQUENCE: 63
```

```
Gly Cys Cys Ser Asp Pro Arg Cys Ala Trp Arg Cys
1               5                   10

<210> SEQ ID NO 64
<211> LENGTH: 329
<212> TYPE: DNA
<213> ORGANISM: Simian vacuolating virus 40

<400> SEQUENCE: 64
gtgtgtcagt tagggtgtgg aaagtcccca ggctccccag caggcagaag tatgcaaagc      60
atgcatctca attagtcagc aaccaggtgt ggaaagtccc caggctcccc agcaggcaga     120
agtatgcaaa gcatgcatct caattagtca gcaaccatag tcccgcccct aactccgccc     180
atcccgcccc taactccgcc cagttccgcc cattctccgc cccatggctg actaattttt     240
tttatttatg cagaggccga ggccgcctcg gcctctgagc tattccagaa gtagtgagga     300
ggcttttttg gagcctaggc ttttgcaaa                                      329

<210> SEQ ID NO 65
<211> LENGTH: 584
<212> TYPE: DNA
<213> ORGANISM: Cytomegalovirus

<400> SEQUENCE: 65
gacattgatt attgactagt tattaatagt aatcaattac ggggtcatta gttcatagcc      60
catatatgga gttccgcgtt acataactta cggtaaatgg cccgcctggc tgaccgccca     120 acgaccccg cccattgacg tcaataatga cgtatgttcc catagtaacg ccaataggga     180
ctttccattg acgtcaatgg gtggagtatt tacggtaaac tgcccacttg gcagtacatc     240
aagtgtatca tatgccaagt acgccccta ttgacgtcaa tgacggtaaa tggcccgcct     300
ggcattatgc ccagtacatg accttatggg actttcctac ttggcagtac atctacgtat     360
tagtcatcgc tattaccatg gtgatgcggt tttggcagta catcaatggg cgtggatagc     420
ggtttgactc acggggattt ccaagtctcc accccattga cgtcaatggg agtttgtttt     480
ggcaccaaaa tcaacgggac tttccaaaat gtcgtaacaa ctccgcccca ttgacgcaaa     540
tgggcggtag gcgtgtacgg tgggaggtct atataagcag agct                     584

<210> SEQ ID NO 66
<211> LENGTH: 31
<212> TYPE: PRT
<213> ORGANISM: Artificial Sequence
<220> FEATURE:
<223> OTHER INFORMATION: A synthetic peptide toxin

<400> SEQUENCE: 66

Ala Cys Ser Lys Lys Trp Glu Tyr Cys Ile Val Pro Ile Leu Gly Phe
1               5                   10                  15

Val Tyr Cys Cys Pro Gly Leu Ile Cys Gly Pro Phe Val Cys Val
                20                  25                  30
```